US012053455B2

(12) United States Patent
Grys et al.

(10) Patent No.: US 12,053,455 B2
(45) Date of Patent: Aug. 6, 2024

(54) ANTIGEN-DRIVEN DETECTION AND TREATMENT OF COCCIDIOIDOMYCOSIS

(71) Applicants: Mayo Foundation for Medical Education and Research, Rochester, MN (US); Arizona Board of Regents on behalf of Arizona State University, Scottsdale, AZ (US)

(72) Inventors: Thomas E. Grys, Scottsdale, AZ (US); Douglas Lake, Scottsdale, AZ (US); Natalie Michelle Mitchell, Phoenix, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 178 days.

(21) Appl. No.: 17/333,255

(22) Filed: May 28, 2021

(65) Prior Publication Data

US 2021/0353598 A1 Nov. 18, 2021

Related U.S. Application Data

(62) Division of application No. 16/310,599, filed as application No. PCT/US2017/037866 on Jun. 16, 2017, now Pat. No. 11,045,451.

(60) Provisional application No. 62/351,073, filed on Jun. 16, 2016.

(51) Int. Cl.
*A61K 31/427* (2006.01)
*A61K 31/4196* (2006.01)
*A61K 31/496* (2006.01)
*A61K 31/506* (2006.01)
*A61K 31/7048* (2006.01)
*G01N 33/569* (2006.01)
*G01N 33/68* (2006.01)

(52) U.S. Cl.
CPC ........ *A61K 31/4196* (2013.01); *A61K 31/427* (2013.01); *A61K 31/496* (2013.01); *A61K 31/506* (2013.01); *A61K 31/7048* (2013.01); *G01N 33/56961* (2013.01); *G01N 33/6848* (2013.01); *G01N 2333/37* (2013.01); *G01N 2800/52* (2013.01)

(58) Field of Classification Search
CPC ......... G01N 33/56961; G01N 2333/37; G01N 33/6848; G01N 2800/52
See application file for complete search history.

(56) References Cited

U.S. PATENT DOCUMENTS 8,163,502 B2  4/2012  Denny et al.
8,911,959 B2 * 12/2014  Lake ...................... G01N 33/68
                                                           435/7.1
11,045,451 B2  6/2021  Grys et al.
2010/0279308 A1  11/2010  Morrow et al.
2013/0164764 A1  6/2013  Lake et al.
2015/0301055 A1  10/2015  Spetzler
2019/0328715 A1  10/2019  Grys et al.

OTHER PUBLICATIONS

Kaushal 2015 (In vitro and In vivo Proteome Analysis of Coccidioides posadasii; Dissertation Presented in Partial Fulfillment of Requirements for the Degree of Doctor of Philosophy; Arizona State University) (Year: 2015).*
"Coccidioides group Sequencing Project, Broad Institute of Harvard and MIT," Retrieved from: <ftp://ftp.broadinstitute.org/pub/annotation/fungi/coccidioides_immitis/>, Jul. 15, 2015, 10 pages.
Ahn et al., "Quantitative Mass Spectrometric Analysis of Glycoproteins Combined with Enrichment Methods," Mass Spectrom. Rev., 2014.
Ampel et al., "Assessment of the Human Cellular Immune Response to T27K, a Coccidioidal Antigen Preparation, by Flow Cytometry of Whole Blood," Med. Mycol., 39(4):315-20, Aug. 2001.
Ampel, "Measurement of Cellular Immunity in Human Coccidioidomycosis," Mycopathologia, 156(4): 247-262, 2003.
Ampel, "The diagnosis of coccidioidomycosis," F1000:2 medicine reports, Jan. 2010.
Binnicker et al., "Detection of *Coccidioides* Species in Clinical Specimens by Real-Time PCR," Journal of clinical microbiology, 45(1):173-178, Jan. 2007.
Blair et al., "Characteristics of patients with mild to moderate primary pulmonary coccidioidomycosis," Emerg. Infect. Dis., 20(6):983-990, Jun. 2014.
Blair et al., "Clinical Specificity of the Enzyme Immunoassay Test for Coccidioidomycosis Varies According to the Reason for Its Performance," Clinical and Vaccine Immunology, 20(1):95-98, Jan. 2013.
Blair et al., "Serologic Testing for Symptomatic Coccidioidomycosis in Immunocompetent and Immunosuppressed hosts," Mycopathologia, 162(5):317-324, Nov. 2006.
Brown et al., "Coccidioidomycosis: Epidemiology," Clin. Epidemiol., 5:185-97, Jun. 2013.
Burnie et al., "Fungal Heat-Shock Proteins in Human Disease," FEMS Microbiol. Rev., 30(1):53-88, Jan. 2006.
Chang et al., "Testing for coccidioidomycosis among patients with community-acquired pneumonia.," Emerging infectious diseases, 14(7):1053, Jul. 2008.
Chowdhury et al., "A Survey of Lectin Reactivity to Coccidioides in Infected Lung Tissue and Identification of Lectin-Binding Coccidioidal Glycoproteins," Poster, Presented at AAAS, San Diego, CA, Feb. 12-16, 2015, 1 page.

(Continued)

*Primary Examiner* — Mary Maille Lyons
(74) *Attorney, Agent, or Firm* — Fish & Richardson P.C.

(57) ABSTRACT

Materials and methods for detecting and treating Coccidioidomycosis (Valley Fever) are provided herein. For example, materials and methods for enriching and detecting biomarker antigens (e.g., polypeptides and/or glycans) from *Coccidioides immitis* and *Coccidioides posadasii*, the fungi that cause Valley Fever, are described herein, as are methods for treating an individual for Valley Fever based on the results of the described detection methods.

6 Claims, 10 Drawing Sheets

(56) References Cited

OTHER PUBLICATIONS

Chowdhury et al., "Abstract: A survey of Lectin Reactivity to Coccidioides in Infected Human Lung Tissue," Presented at 58th Coccidioides Study Group Meeting, Apr. 5, 2014, 1 page.
Cox and Britt, "Antigenic Identity of Biologically Active Antigens in Coccidioidin and Spherulin," Infect Immun., 55(11):2590-2596, Nov. 1987.
Durkin et al., "Detection of Coccidioides Antigenemia following Dissociation of Immune Complexes," Clin. Vaccine Immunol., 16(10):1453-1456, Aug. 2009.
Durkin et al., "Diagnosis of Coccidioidomycosis with Use of the Coccidioides Antigen Enzyme Immunoassay," Clin. Infect. Dis., 47(8):e69-73, Oct. 2008.
Fisher et al., "Coccidioides Niches and Habitat Parameters in the Southwestern United States: A Matter of Scale," Ann. NY Acad. Sci., 1111:47-72, 2007.
GenBank Accession No. DS268110., "*Coccidioides posadasii* RMSCC 3488 Supercont1.2 Genomic Scaffold, Whole Genome Shotgun Sequence," dated Jun. 29, 2015, 2 pages.
GenBank Accession No. DS268111.1, "*Coccioides posadasii* RMSCC 3488 Supercont 1.3 Genomic Scaffold, Whole Genome Shotgun Sequence," dated Jun. 29, 2015, 2 pages.
GenBank Accession No. DS268112.1, "*Coccidioides posadasii* RMSCC 3488 Supercont1.4 Genomic Scaffold, Whole Genome Shotgun Sequence," dated Jun. 29, 2015, 2 pages.
GenBank Accession No. DS268114.1, "*Coccidioides posadasii* RMSCC 3488 Supercont1.6 Genomic Scaffold, Whole Genome Shotgun Sequence," dated Jun. 29, 2015, 2 pages.
GenBank Accession No. GL36486.1, "*Coccidioides posadasii* str. *silveira* Unplaced Genomic Scaffold Supercont2.1, Whole Genome Shotgun Sequence," dated Jul. 25, 2016, 2 pages.
GenBank Accession No. GL36504.1, "*Coccidioides posadasii* str. *silveira* Unplaced Genomic Supercont2.19, Whole Genome Shotgun Sequence," dated Jul. 25, 2016, 2 pages.
GenBank Accession No. GL636489.1, "*Coccidioides posadasii* str. *silveira* Unplaced Genomic Scaffold Supercont.2.4, Whole Genome Shotgun Sequence," dated Jul. 25, 2016, 2 pages.
GenBank Accession No. GL636490.1, "*Coccidioides posadasii* str. *silveira* Unplaced Genomic Scaffold Supercont.2.5, Whole Genome Shotgun Sequence," dated Jul. 25, 2016, 2 pages.
GenBank Accession No. GL636504.1, "*Coccidioides posadasii* str. *silveira* Unplaced Genomic Scaffold Supercont2.19, Whole Genome Shotgun Sequence," dated Jul. 2016, 27 pages.
Goto, "Protein O-glycosylation in Fungi: Diverse Structures and Multiple Functions," Biosci. Biotechnol. Biochem., 71(6):1415-1427, Jun. 2007.
Grys et al., "Total and Lectin-Binding Proteome of Spherulin from *Coccidioides posadasii*," J. Proteome Res., 15(10):3463-3472, Oct. 2016.
Johnson et al., "A Reformulated Spherule-Derived Coccidioidin (Spherusol) to Detect Delayed-Type Hypersensitivity in Coccidioidomycosis," Mycopathologia 174(5-6):353-358, Jun. 2012.
Kaushal, "In vitro and In vivo Proteome Analysis of Coccidioides posadassii," A dissertation Presented in Partial Fulfillment of the Requirements for the Degree Doctor of Philosophy, Arizona State University, 84 pages, Dec. 2015.
Keller et al., "Empirical Statistical Model to Estimate the Accuracy of Peptide Identifications Made by MS/MS and Database Search," Anal. Chem., 74(20):5383-5392, Oct. 2002.
Kessner et al., "ProteoWizard: open source software for rapid proteomics tools development," Bioinformatics, 24(21):2534-2536, Jul. 2008.
Kim et al., "Coccidioidal Pneumonia, Phoenix, Arizona, USA, 2000-2004," Emerging infectious diseases, 15(3):397-40, Mar. 2009.
Laboratories, V. Table of Lectin Properties. 2014 [cited 2014 Nov. 12, 2014]; Available from: http://www.vectorlabs.com/data/protocols/K4-K7.pdf.

Ma et al., "ID Picker 2.0: Improved Protein Assembly with High Discrimination Peptide Identification Filtering," J. Proteome Res., 8(8):3872-3881, Aug. 2009.
Martin et al., "Biochemistry and molecular biology of exocellular fungal β-(1, 3)-and β-(1, 6)-glucanases," FEMS Microbiol. Rev., 31(2):168-192, Mar. 2007.
Mora-Montes et al., "A Multifunctional Mannosyltransferase Family in *Candida albicans* Determines Cell Wall Mannan Structure and Host-Fungus Interactions," Journal of Bio. Chem., 285(16):12087-12095, Apr. 2010.
Neafsey et al., "Population Genomic Sequencing of Coccidioides Fungi Reveals Recent Hybridization and Transposon Control," Genome Res., 20(7):938-946, Jul. 2010.
Nesvizhskii et al., "A Statistical Model for Identifying Proteins by Tandem Mass Spectrometry," Anal. Chem., 75(17):4646-4658, Sep. 2003.
Orsborn et al., "Protein expression profiling of *Coccidioides posadasii* by two-dimensional differential in-gel electrophoresis and evaluation of a newly recognized peroxisomal matrix protein as a recombinant vaccine candidate," Infect. Inmun., 74(3):1865-1872, 2006.
Pappagianis and Zimmer, "Serology of Coccidioidomycosis," Clin. Microbiol. Rev., 3(3):247-268, Jul. 1990.
PCT International Preliminary Report on Patentability in International Appln. No. PCT/US2017/037866 dated Dec. 18, 2018, 10 pages.
PCT International Search Report and Written Opinion in International Appln. No.PCT/US 17/37866 dated Oct. 27, 2017, 13 pages.
Schiess et al., "Targeted Proteomic Strategy for Clinical Biomarker Discovery," Mol. Oncol., 3(1):33-44, Feb. 2009.
Sharpton et al., "Comparative Genomic Analyses of the Human Fungal Pathogens Coccidioides and their Relatives," Genome Res., 19(10):1722-1731, Oct. 2009.
Sunenshine et al., "Public Health Surveillance for Coccidioidomycosis in Arizona" Ann. NY Acad. Sci., 1111:96-102, Sep. 2007.
Tabb et al., "MyriMathc: Highly Accurate Tandem Mass Spectral Peptide Identification by Multivariate Hypergeometric Analysis," J. Proteome Res., 6(2):654-661, Feb. 2007.
Tsang et al., "Enhanced Surveillance of Coccidioidomycosis," Arizona, USA, 2007-2008, Emerging infectious diseases, 16(11):1738-1744, Nov. 2010.
Valdivia et al., "Coccidioidomycosis as a Common Cause of Community-Acquired Pneumonia," Emerging infectious disease, 12(6):958-962, Jun. 2006.
Varki et al., eds. Essentials of Glycobiology. Second ed. vol. 1. Cold Spring Harbor Laboratory Press: Cold Spring Harbor, NY. 263-279, 2009.
Vucicevic et al., "The Utility of Coccidioides Polymerase Chain Reaction Testing in the Clinical Setting," Mycopathologia, 170(5):345-351 Jun. 2010.
Yang et al., "Molecular Cloning and Characterization of the *Coccidioides immitis* Complement Fixation/chitinase Antigen," Infect. Immun., 64(6):1992-1997, Jun. 1996.
Zhang et al., "Proteomic Parsimony through Bipartite Graph Analysis Improves Accuracy and Transparency," Journal of proteome research, 6(9):3549-3557, Sep. 2007.
Ampel, "Coccidioidomycosis in persons infected with HIV-1," Ann NY Acad Sci, Sep. 2007, 1111:336-342.
Anderson et al., "The human plasma proteome: History, character, and diagnostic prospects," Mol Cell Proteomics, Nov. 2002, 1(11):845-867.
Centers for Disease Control and Prevention (CDC), "Increase in reported coccidioidomycosis—United States, 1998-2011," Morbidity and Mortality Weekly Report (MMWR), Mar. 2013, 62(12):217-221.
Centers for Disease Control and Prevention (CDC), "Notice to readers: Final 2012 reports of nationally notifiable infectious diseases," Morbidity and Mortality Weekly Report (MMWR), Aug. 2013, 62(33):669-82.
Champer et al., "Protein targets for broad-spectrum mycosis vaccines: Quantitative proteomic analysis of aspergillus and Coccidioides and comparisons with other fungal pathogens," Ann NY Acad Sci, Dec. 2012, 1273:44-51.

(56) References Cited

OTHER PUBLICATIONS

Cole et al., "Antigen complex of Coccidioides immitis which elicits a precipitin antibody response in patients," Infect Immun, Jul. 1991, 59(7):2434-246.
Cox et al., "Coccidioidomycosis: Host response and vaccine development," Clin Microbiol Rev, Oct. 2004, 17(4):804-839.
Dixon, "Coccidioides immitis as a select agent of bioterrorism," J Appl Microbiol, Oct. 2001, 91(4):602-605.
Galgiani et al., "Coccidioidomycosis," Clin. Infect. Dis., Nov. 2005, 41(9):1217-1223.
Galgiani et al., "New serologic tests for early detection of coccidioidomycosis," J Infect Dis, Mar. 1991, 163(3):671-674.
GenBank Accession No. DS268113.1, "Coccidioides Posadasii RMSCC 3488 Supercont1.5 Genomic Scaffold, Whole Genome Shotgun Sequence," dated Jun. 29, 2015, 2 pages.
GenBank Accession No. GL636493.1, "Coccidioides Posadasii str. Silveira Unplaced Genomic Scaffold Supercont.2.8, Whole Genome Shotgun Sequence," dated Jul. 25, 2016, 2 pages.
Guo et al., "An efficient procedure for protein extraction from formalin-fixed, paraffin-embedded tissues for reverse phase protein arrays," Proteome Sci., Sep. 2012, 10(1):56.
Hector et al., "The public health impact of coccidioidomycosis in Arizona and California," Int J Environ Res Public Health, Apr. 2011, 8(4):1150-1173.
Hung et al., "A major cell surface antigen of Coccidioides immitis which elicits both humoral and cellular immune responses," Infect Immun, Feb. 2000, 68(2):584-593.
Hurtgen et al., "Construction and evaluation of a novel recombinant T cell epitope-based vaccine against coccidioidomycosis," Infect Immun, Nov. 2012, 80(11):3960-3974.
Kirsch et al., "Evaluation of Coccidioides antigen detection in dogs with coccidioidomycosis," Clin Vaccine Immunol, Mar. 2012, 19(3):343-345.
Kruse et al., "Isolation of tube precipitin antibody-reactive fractions of Coccidioides immitis, " Infect Immun, Jan. 1990, 58(1): 169-178.
Maes et al., "Analysis of the formalin-fixed paraffin-embedded tissue proteome: Pitfalls, challenges, and future prospectives," Amino Acids, Aug. 2013, 45(2):205-218.
Maes et al., "Proteomic analysis of formalin-fixed paraffin-embedded colorectal cancer tissue using tandem mass tag protein labeling," Mol Biosyst, Nov. 2013, 9(11):2686-2695.
Mahboob et al., "Is isolation of comprehensive human plasma peptidomes an achievable quest?" J Proteomics, Sep. 2015, 127(Pt B):300-309.
Marimuthu et al., "A comprehensive map of the human urinary proteome," J Proteome Res, Jun. 2011, 10(6):2734-2743.
Marsden-Haug et al., "Coccidioides immitis identified in soil outside of its known range—washington, 2013," Morbidity and Mortality Weekly Report (MMWR), May 2014, 63(20):450.
Masannat et al., "Coccidioidomycosis in patients with HIV-1 infection in the era of potent antiretroviral therapy," Clin Infect Dis, Jan. 2010, 50(1):1-7.
Nanjappa et al., "Plasma proteome database as a resource for proteomics research: 2014 update," Nucleic Acids Res, Jan. 2014, 42(Database issue): D959-D965.
Nguyen et al., "Recent advances in our understanding of the environmental, epidemiological, immunological, and clinical dimensions of coccidioidomycosis," Clin Microbiol Rev, Jul. 2013, 26(3):505-525.
Oliveros, "Venny. An interactive tool for comparing lists with Venn's diagrams," available no later than Jun. 16, 2017, retrieved from URL<https://bioinfogp.cnb.csic.es/tools/venny/index.html>, 1 page.
Paulo et al., "A proteomic comparison of formalin-fixed paraffin-embedded pancreatic tissue from autoimmune pancreatitis, chronic pancreatitis, and pancreatic cancer," JOP, Jul. 2013, 14(4):405-414.
Pisitkun et al., "Tandem mass spectrometry in physiology," Physiology, Dec. 2007, 22:390-400.
Richter et al., "Composition of the peptide fraction in human blood plasma: Database of circulating human peptides," J Chromatogr B Biomed Sci Appl, Apr. 1999, 726(1-2):25-35.
Saubolle, "Laboratory aspects in the diagnosis of coccidioidomycosis," Ann NY Acad Sci, Sep. 2007, 1111:301-314.
Shi et al., "Complete solubilization of formalin-fixed, paraffin embedded tissue may improve proteomic studies," Proteomics Clin Appl, Apr. 2013, 7(3-4):264-272.
Sigrist et al., "PROSITE: a documented database using patterns and profiles as motif descriptors," Brief Bioinform., Sep. 2002, 3(3):265-274.
Sprung et al., "Equivalence of protein inventories obtained from formalin-fixed paraffin-embedded and frozen tissue in multidimensional liquid chromatography-tandem mass spectrometry shotgun proteomic analysis," Mol Cell Proteomics, Aug. 2009, 8(8): 1988-1998.
Tamerius et al., "Coccidioidomycosis incidence in arizona predicted by seasonal precipitation," PLoS One, Jun. 2011, 6(6):e21009.
Tanca et al., "Critical comparison of sample preparation strategies for shotgun proteomic analysis of formalin-fixed, paraffin-embedded samples: Insights from liver tissue," Clin Proteomics, Jul. 2014, 11(1):28.
Thompson et al., "Call for a California coccidioidomycosis consortium to face the top ten challenges posed by a recalcitrant regional disease," Mycopathologia, Feb. 2015, 179(1-2):1-9.
Vincenti et al., "The proteomics of formalin-fixed wax-embedded tissue," Clin Biochem, Apr. 2013, 46(6):546-551.
Viriyakosol et al., "Gene expression in human fungal pathogen Coccidioides immitis changes as arthroconidia differentiate into spherules and mature," BMC Microbiol, May 2013, 13:121.
Wakabayashi et al., "Phosphoproteome analysis of formalin-fixed and paraffin-embedded tissue sections mounted on microscope slides," J Proteome Res, Feb. 2014, 13(2):915-924.
Weiner, "Antigenemia detected in human coccidioidomycosis," J Clin Microbiol, Jul. 1983, 18(1): 136-142.
Whiston et al., "Genomics in Coccidioides: Insights into evolution, ecology, and pathogenesis," Med Mycol, Feb. 2014, 52(2):149-155.
Yuan et al., "Possible role of a proteinase in endosporulation of Coccidioides immitis," Infect Immun, Jun. 1988, 56(6):1551-1559.

* cited by examiner

PATIENT 1 | No lectin | GSL-II | sWGA
PATIENT 2 | No lectin | GSL-II | sWGA
PATIENT 3 | No lectin | GSL-II | sWGA
PATIENT 4 | No lectin | GSL-II | sWGA
PATIENT 5 | No lectin | GSL-II | sWGA
PATIENT 6 | No lectin | GSL-II | sWGA
PATIENT 7 | No lectin | GSL-II | sWGA

Patient 1   Patient 2

134 *Coccidioides* proteins found in total

FIG. 8

Acute   Chronic

594
(2%)

16303
(53.6%)

6
(0%)

6
(0%)

286
(0.9%)

45
(0.1%)

0
(0%)

2
(0%)

13090
(43%)

0
(0%)

0
(0%)

84
(0.3%)

0
(0%)

3
(0%)

5
(0%)

Disseminated           CDN Ag

FIG. 9

| Scan ID | Retention Time | Prec. m/z | charge | Glycan ID | Glycan mass | Molecular Formula |
|---|---|---|---|---|---|---|
| Scan9122@780.708_3 | 38.5598 | 780.708 | 3 | SGI01809 | 2274.861924054 | $C_{88}H_{146}O_{60}N_8$ |

ANTIGEN-DRIVEN DETECTION AND TREATMENT OF COCCIDIOIDOMYCOSIS

CROSS-REFERENCE TO RELATED APPLICATIONS

This application is a divisional of U.S. application Ser. No. 16/310,599 filed Dec. 17, 2018, which is a National Stage application under 35 U.S.C. § 371 of International Application No. PCT/US2017/037866 having an International Filing Date of Jun. 16, 2017, which claims benefit of priority from U.S. Application Ser. No. 62/351,073, filed on Jun. 16, 2016.

TECHNICAL FIELD

This document relates to materials and methods for detecting and treating Valley Fever.

BACKGROUND

Coccidioidomycosis [Valley Fever (VF)] is a respiratory disease caused by the inhalation of spores from the soil-dwelling fungi, *Coccidioides immitis* and *Coccidioides posadasii*. VF is endemic to the Southwestern U.S. and northern Mexico. In 2012, for example, 73% of the cases reported in the U.S. were reported in Arizona, and 25% were reported in California. The occurrence of VF has increased dramatically since the late 1990's. About 40% of affected individuals experience symptoms such as cough, fever, fatigue, rash, and night sweats, and about 5% have severe pneumonia and require appropriate treatment. In fact, VF has been reported to cause up to 30% of community-acquired pneumonia (CAP) in endemic regions (Blair et al., *Emerg Infect Dis* 20(6):983-990, 2014). Further, in about 1% of individuals infected with VF, the organism disseminates from the lungs to other parts of the body, causing a life-threatening systemic infection. Primary infection or reactivation of latent infection are higher risks in patients who are immunocompromised (e.g., transplant recipients or people with AIDS), or who are taking immune-modifying drugs such as TNF-α inhibitors.

In the environment, *Coccidioides* spp. exists as a mold with septate hyphae, which fragment into arthroconidia that are easily aerosolized. These arthroconidia are inhaled and settle into the lungs, eventually becoming spherules that divide internally until they are filled with endospores. When the spherules rupture, the endospores are released, disseminating into surrounding tissue and developing into new spherules that repeat the cycle.

SUMMARY

Diagnosing VF from symptoms alone can be difficult, if not impossible, due to similarities between the symptoms of VF and symptoms associated with CAP caused by other organisms. Unlike many other etiologies of CAP (bacteria and viruses) that are either self-limited or treated empirically, VF is not responsive to antibacterial or anti-viral drugs, and symptoms may persist for months. The mean time to diagnosis of VF is about 2-3 months (Sunenshine et al., *Ann NY Acad Sci* 1111:96-102, 2007), a time period that may include one or more empiric antibacterial or anti-viral therapy regimens in the setting of persisting or worsening symptoms and often multiple visits to a healthcare facility. VF is typically not high in the differential diagnosis, so testing is often not performed. This is true even in endemic areas, since physicians practicing in such locations are likely to have been trained in non-endemic areas and are not familiar with recognizing the disease or testing strategies.

Moreover, even when VF testing is performed, antibodies against the fungus may not be produced at detectable levels by the body for 4-10 weeks. Therefore, early negative test results may occur and repeated antibody testing may be performed. Even though there are three methods of antibody detection (complement fixation [CF], immunodiffusion [ID], and enzyme immunoassay [EIA]), not all patients with VF will test positive by all antibody assays. Some patients fail to ever mount an antibody response, rendering antibody assays useless. Antibody testing is only a proxy of disease and immunity, since the functionally effective immune response is cell-mediated, rather than via antibodies (humoral response). Positive results by antibody tests may persist well after clinical improvement. Thus, when a complex patient (e.g., a transplant recipient) is being treated, it can be difficult to gain definitive laboratory evidence of disease resolution, particularly when non-specific symptoms consistent with VF or other diseases remain. Culture is inexpensive but slow (ranging from several to many days), and PCR is rapid but expensive. Culture and PCR have similar sensitivity, but both are limited in that they require a sputum or bronchoalveolar lavage (BAL) specimen to send to the laboratory. Most patients with VF have a dry cough and are not able to produce sputum, obviating the utility of culture and PCR.

Thus, this document provides improved methods for detecting and treating VF, based at least in part on the discovery that direct detection of fungal components (as opposed to detection of antibodies) from body fluids can provide a definitive diagnosis. As described herein, for example, certain lectins (carbohydrate-binding proteins) have differential binding properties to coccidioidal antigens (polypeptides and/or glycans), due to the fact that many fungal glycosylation patterns are distinct from mammalian glycosylation patterns. These differential binding properties can serve as a tool for improved detection and treatment of VF. Thus, this document is based, at least in part, on the identification of a common subset of polypeptide and/or glycan antigens that are found in patients with active VF that bind to particular lectins [*Griffonia simplicifolia* II lectin (GSLII) and/or succinylated Wheat Germ Agglutinin (sWGA)] and/or antibodies specific to *Coccidioides* antigens, but are not found in control patients (e.g., healthy subjects or patients known to have non-coccidioidal community-acquired pneumonia). The lectins and/or antibodies may be used in an enzyme immunoassay format, or to partially purify antigens for detection by a mass spectrometry assay such as matrix associated laser desorption ionization-time of flight (MALDI-TOF) mass spectrometry.

In some embodiments, therefore, this document provides assays that include detecting antigens from *C. immitis* and/or *C. posadasii*, the causative agents of VF. The assays utilize lectins to selectively purify fungal antigens (e.g., peptides and/or glycans) from body fluids such as blood, plasma, serum, urine, bronchoalveolar lavage, saliva, etc. The lectin approach can be useful because glycosylation patterns may be quite specific to particular species or organisms. For example, proteins from fungal organisms often have mannose-rich glycosylation, whereas human proteins often have terminal sialic acid residues in their carbohydrate groups. The methods provided herein use mass spectrometry for sensitive and specific detection of the fungal antigens (e.g., polypeptides and/or glycans). In some cases, the methods can be adapted to include the use of MALDI-TOF mass spectrometry of the type employed for rapid and low cost identification of bacteria from culture plates (e.g., from Bruker Daltonics, Billerica, MA, and BioMérieuc, Marcy-l'Étoile, France).

In one aspect, this document features a method for tailoring or altering treatment for a subject presenting with, and optionally undergoing antimicrobial treatment for, one or more symptoms of community-acquired pneumonia, or a subject with one or more symptoms of invasive fungal infection. The method includes detecting one or more antigens (e.g., polypeptides and/or glycans) of *Coccidioides immitis* and/or *Coccidioides posadasii* in a body fluid sample from the subject, wherein the detecting includes lectin-based or antibody-based enrichment of *C. immitis* and/or *C. posadasii* antigens, and detection of one or more of the antigens; and stopping the antibacterial or anti-viral treatment, initiating antifungal treatment, or stopping the antibacterial or anti-viral treatment and initiating antifungal treatment. The antifungal treatment can include administration of fluconazole, ketoconazole, itraconazole, voriconazole, posaconazole, isavuconazole, amphotericin, or other available antifungal agents. The detecting can include the use of common immunoassay formats, such as enzyme immunoassay (EIA), enzyme-linked immunoabsorbant assay (ELISA), line immunochromatographic assays (LIAs), and the like, whereby an antibody is immobilized on a surface (e.g., plastic or a paper filter), and a body fluid or affinity-enriched body fluid is contacted with the immobilized antibody and then detected by another binding agent (e.g., antibody or lectin). The detecting also can include using mass spectrometry. The mass spectrometry can generate mass/charge peaks that are representative for infection with *Coccidioides* fungus, or that supply data that include sequences of peptides or evidence of glycan structures that match *Coccidioides* sequences/structures. The mass spectrometry can be matrix associated laser desorption ionization time of flight (MALDI-TOF) mass spectrometry, or liquid chromatography followed by tandem mass spectrometry (LC-MS/MS). The detecting can include using one or more antibodies against one or more *Coccidioides* antigens (e.g., peptides and/or glycans). The detecting can include using one or more lectins that bind to the one or more antigens. The one or more lectins can be succinylated Wheat Germ Agglutinin (sWGA), *Griffonia simplicifolia* II lectin (GSLII), Wheat Germ Agglutinin (WGA), or a combination of WGA, sWGA, and/or GSLII, or other lectins that bind exclusively to *Coccidioides* antigens such as N-acetyl glucosamine (GlcNAc). The detecting can include using one or more lectins that bind to both human and *Coccidioides* antigens. The one or more lectins can be Concanavalin A (Con A), *Erythrina* crystagalli Lectin (ECL), and *Pisum sativum* Agglutinin (PSA). The lectin can bind to human antigens and negatively enrich *Coccidioides* antigens by reducing the number or percentage of human antigens present in the body fluid from the subject. In some embodiments, the negatively enriching lectin can include one or more of Con A, *Datura stramonium* Lectin (DSL), ECL, *Griffonia simplicifolia* Lectin I (GSLI), Jacalin (JAC), Len culinaris Lectin (LCA), Peanut Agglutinun (PNA), *Phaseolus vulgaris* Erythroagglutinin (PVE), *Phaseolus vulgaris* Leukoagglutinin (PVL), PSA, *Ricinus communis* Agglutinin (RCA I), *Solanum tuberosum* Lectin (STL), Soybean Agglutinin (SBA), *Ulex europaeus* Agglutinin I (UEA I), and *Vicia villosa* Lectin (VVL). The body fluid can include blood, plasma, serum, urine, saliva, sputum, induced sputum, nasal washing, bronchial washing, bronchial brushing, tracheal secretions, bronchoalveolar lavage, or cerebrospinal fluid. The volume of the body fluid sample can range from 0.02 mL to 200 mL. The body fluid sample can be contacted with the lectin(s) for 1 second to 48 hours.

In another aspect, this document features a method for altering the treatment of a subject being considered for immunosuppressive therapy, or a subject with symptoms of meningitis. The method can include detecting one or more antigens (e.g., one or more polypeptides and/or glycans) of *Coccidioides immitis* and/or *Coccidioides posadasii* in a body fluid sample from the subject, where the detecting includes lectin-based and/or antibody-based enrichment of *C. immitis* and/or *C. posadasii* antigens, and detection of one or more of the antigens or their components (e.g., polypeptides or glycans), and stopping or delaying administration of immunosuppressive therapy. The immunosuppressive therapy can be for solid organ or hematopoietic stem cell transplant. The immunosuppressive therapy can include administration of one or more corticosteroids or TNF-alpha inhibitors, one or more glucocorticoids or other immunosuppressive biological agents. In some embodiments, the immunosuppressive therapy can include administration of cyclosporine, tacrolimus, sirolimus, mycophenolate, muromonab-CD3, antithymocyte globulin, rituximab, or thalidomide. The method can further include administering an anti-fungal agent to the subject. The anti-fungal agent can include fluconazole, ketoconazole, itraconazole, voriconazole, posaconazole, isavuconazole, or amphotericin. The detecting can include using mass spectrometry. The mass spectrometry can generate mass/charge peaks representing antigens (polypeptides and/or glycans) that are associated with infection by *Coccidioides* fungus, or that supply data such as sequences or structures of antigens that match *Coccidioides* antigens. The mass spectrometry can be MALDI-TOF mass spectrometry or LC-MS/MS. The detecting can include using one or more antibodies against one or more *Coccidioides* antigens. The lectin can be sWGA, GSLII, WGA, or a combination of WGA, sWGA, and/or GSLII. The detecting can include using one or more lectins that bind to both human and *Coccidioides* antigens. The one or more lectins can be Con A, ECL, and PSA. The detecting can include using one or more lectins that bind to antigens. The one or more lectins can bind to human antigens and enrich *Coccidioides* antigens by reducing the number or percentage of human antigens present in a specimen. In some embodiments, the lectin can include one or more of Con A, DSL, ECL, GSLI, JAC, LCA, PNA, PVE, PVL, PSA, RCA I, STL, SBA, UEA I, and VVL. The body fluid sample can include blood, plasma, serum, urine, saliva, sputum, induced sputum, nasal washing, bronchial washing, bronchial brushing, tracheal secretions, bronchoalveolar lavage, or cerebrospinal fluid. The volume of the body fluid sample can be from 0.02 mL to 200 mL. The body fluid sample can be contacted with the lectin(s) for 1 second to 48 hours.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 includes lectin-based IHC micrographs from VF patients. Biotinylated lectins were incubated with infected lung tissues from seven patients. Darker areas indicate reactivity of lectin. GSLII and sWGA reacted positively and specifically to endospores and spherules, and not to the adjacent human lung tissue.

FIG. 8 is a Venn diagram indicating counts of common coccidioidal proteins in patient plasma. Ninety-one proteins and their isoforms (counting proteins represented by two or more tryptic peptides) were commonly present in plasma acquired from patient 1 and patient 2.

FIG. 9 is Venn diagram of unique glycan precursor m/z values in six positive Coccidioidomycosis patients and *Coccidioides* fungal lysate (CDN Ag), that were not identified in the six negative control samples.

FIG. 10A is a diagram indicating M/z versus intensity of parent peak 780.708 when fragmented into MS/MS spectra. MS/MS spectra that matched theoretical glycan fragment masses are shown with their corresponding sugar structures. FIG. 10B is a diagram generated after glycan fragments from MS/MS spectra were compiled into a best fit parent glycan molecule. FIG. 10C shows exported results data for the parent scan, showing the retention time that the molecule eluted off the column, its charge state, glycan identification number, theoretical glycan parent mass, and molecular formula.

DETAILED DESCRIPTION

Figure 1:
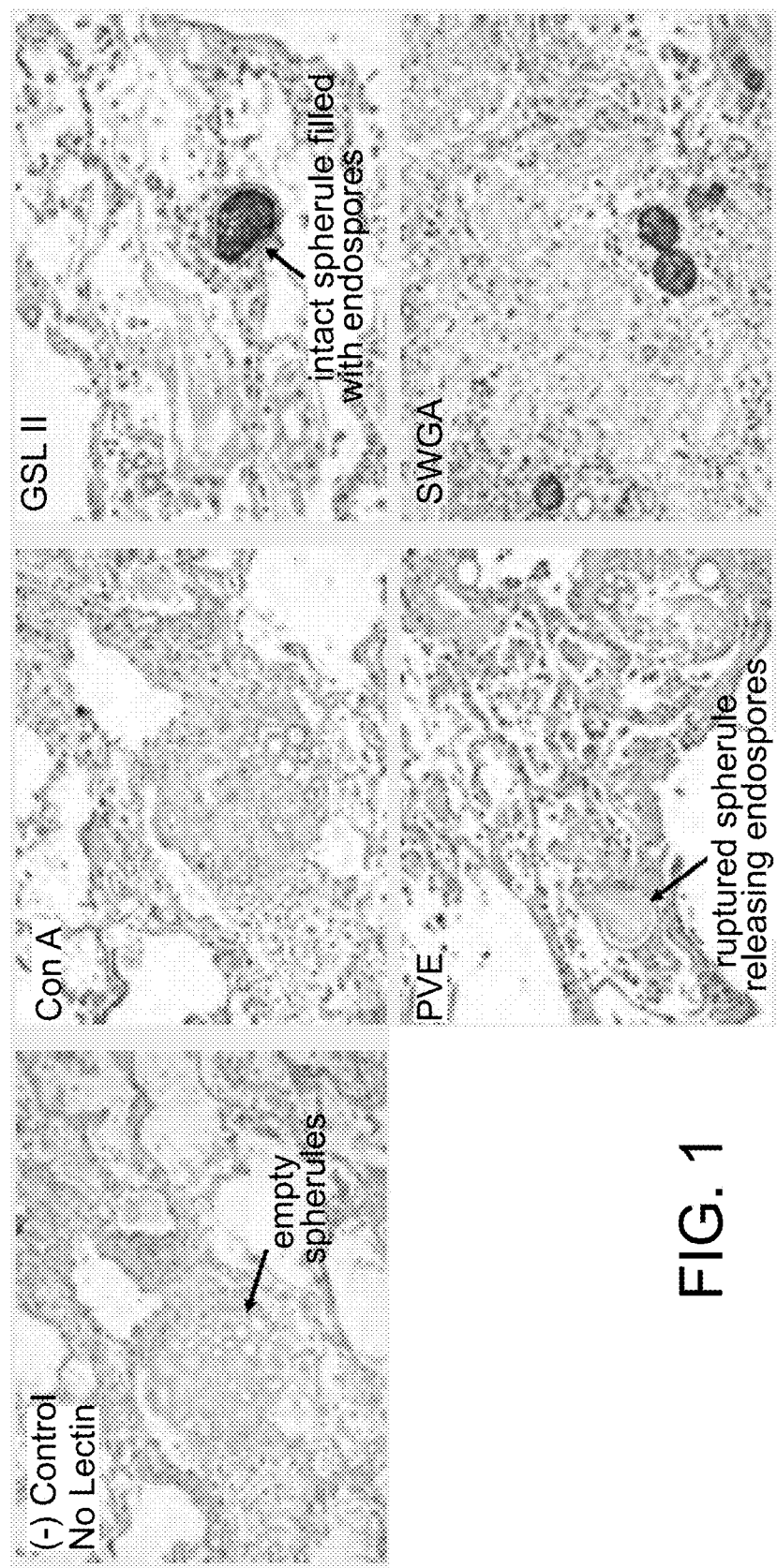
FIG. 1 includes selected micrographs of infected human lung tissue stained with lectins by immunohistochemistry. Con A: Concanavalin A, GSL II: *Griffonia simplicifolia* lectin II, PVE=*Phaseolus vulgaris* erythroagglutinin, SWGA=succinylated wheat germ agglutinin. Darker areas indicate reactivity of the lectin with the fungus.

This document is based, at least in part, on the development of sensitive and specific methods of detecting VF antigens (e.g., peptides and/or glycans). In some embodiments, the methods provided herein can include contacting a biological sample (e.g., a sample of bodily fluid) from a subject (e.g., a human subject or a non-human mammal such as a canine, feline, rodent, equine, bovine, ovine, or porcine mammal, or a mammal in the *Delphinoidea* superfamily, where the subject has one or more symptoms of CAP and/or VF) with fixed lectins or antibodies so as to allow purification through a lectin affinity column or lectin-linked magnetic particles, for example. Bound VF antigens can be eluted from the lectin or antibody and digested with a protease and/or a glycosidase to generate peptide and/or glycan fragments. The fragments can be analyzed by, for example, mass spectrometry, to allow specific characterization of mass/charge signatures and, in some cases, amino acid or glycan sequences/structures. In some embodiments, for example, a method as provided herein can include running a urine sample through a sWGA column, eluting the bound antigens (e.g., peptides and/or glycans), and using mass spectrometry to identify specific the antigens. In some cases, the eluted antigens can be digested with trypsin prior to mass spectroscopy. Mass spectrometry has a high analytical specificity, as specific mass/charge peaks typically are highly reproducible and represent particular fragments of specific antigens. Thus, the identification of particular mass/charge signatures that are specific to one or more *Coccidioides* antigens can be highly predictive of infection.

As described herein, the use of such methods with samples from patients known to have active VF resulted in the detection of 91 fungal proteins (see, FIG. 8) and 25 glycans (see, TABLE 1). Thus, the methods provided herein can provide sensitive and specific detection of VF, which can lead to altered or more efficient treatment of affected individuals. For example, treatment of patients with antibiotics may be discontinued once the patients are affirmatively diagnosed with VF. Not only would such a treatment alteration benefit the patients by targeting the correct pathogen, but also the discontinuation of antibiotic treatment can reduce the risk of *C. difficile* infection, and also can reduce the occurrence of antibiotic side effects such as nausea, diarrhea, hearing loss, and risk of tendon rupture. Further, the discontinuation of unnecessary antibacterial or anti-viral drugs is a broad benefit to public health, as it lowers the chance of developing resistant organisms. In addition to Coccidioidomycosis, the methods described herein may be applicable to the detection of antigens (e.g., polypeptides and/or glycans) from other pathogens, including fungi such as, without limitation, *Blastomyces* sp., *Histoplasma* sp., *Aspergillus* sp., *Candida* sp., and *Mucor* sp.

The methods provided herein can be used to direct treatment decisions for patients presenting with, and in some cases undergoing antibacterial or anti-viral treatment for, one or more symptoms of invasive fungal infection or CAP. Treatment decisions based on the results provided by this method may include, discontinuation of antibacterial drugs that can be a risk factor for infection by *Clostridium difficile* and can cause side effects such as nausea, diarrhea, hearing loss, and tendon rupture. Antibacterial drugs are currently over-utilized, leading to the emergence of resistant organisms. In addition or alternatively, treatment decisions can include the initiation or continuation of antifungal drugs against *Coccidioides*, such as fluconazole and/or voriconazole. In addition, an affirmative diagnosis of VF can allow practitioners to cease additional testing for other etiologies of infection, providing cost-savings for the patient and the health care facility, and avoiding potential false-positive testing that might result in unnecessary treatment.

Thus, in some embodiments, this document provides methods that include detecting one or more antigens, such as one or more peptides or glycans, or a combination of one or more peptides and one or more glycans, of *Coccidioides immitis* and/or *Coccidioides posadasii* in a biological sample from a subject (e.g., a body fluid sample from a subject exhibiting one or more symptoms of CAP or invasive fungal infection), where the detecting includes (i) lectin-based or antibody-based enrichment of *C. immitis* and/or *C. posadasii* antigens and (ii) detection of one or more of the antigens or fragments thereof, and stopping antibacterial or anti-viral treatment if the subject is undergoing such treatment, initiating antifungal treatment, or stopping antibacterial or anti-viral treatment and initiating antifungal treatment. Any suitable antifungal treatment that is effective against *Coccidioides* can be used to treat a subject diagnosed with VF using the methods described herein. Useful antifungal treatments can include, for example, fluconazole, ketoconazole, itraconazole, voriconazole, posaconazole, isavuconazole, and amphotericin.

This document also provides methods for altering the treatment of patients being considered for immune-modifying therapy, or patients with symptoms of meningitis, where the methods include detecting one or more *C. immitis* and/or *C. posadasii* antigens (e.g., one or more *C. immitis* and/or *C. posadasii* polypeptides, glycans, or a combination thereof) in a biological sample from a patient, based on lectin-based or antibody-based enrichment of *C. immitis* and/or *C. posadasii* antigens, and detecting one or more of the antigens or components thereof. The alteration in treatment may include stopping administration of immunosuppressive therapy (e.g., immunosuppressive therapy for a solid organ or stem cell transplant, administration of steroids or TNF-alpha inhibitors, administration of a glucocorticoid, administration of tumor necrosis factor alpha (TNF-alpha, or administration of one or more of cyclosporine, tacrolimus, sirolimus, mycophenolate, muromonab-CD3, antithymocyte globulin, rituximab, or thalidomide), or delaying administration of such therapy.

As used herein, the term "antigen" can refer to any peptide or glycan from a particular organism (e.g., from a fungus of the *Coccidioides* sp., *Blastomyces* sp., *Histoplasma* sp., *Aspergillus* sp., *Candida* sp., or *Mucor* sp.). As used herein, the term "polypeptide" refers to any chain of amino acids, regardless of length or post-translational modification (e.g., glycosylation or phosphorylation). A polypeptide can be, for example, between 5 and 1000 amino acids in length. In some embodiments, a polypeptide is about 10 to about 50 amino acids in length, about 25 to about 100 amino acids in length, about 50 to about 150 amino acids in length, about 100 to about 200 amino acids in length, about 200 to about 300 amino acids in length, about 300 to about 500 amino acids in length, about 500 to about 750 amino acids in length, or about 750 to about 1000 amino acids in length. The term "polypeptide" therefore encompasses relatively short peptides (e.g., polypeptides that are about 10 to about 25 amino acids in length) as well as full length proteins.

As used herein, the term "glycan" refers to any molecule covalently linked to one or more monosaccharide molecules, regardless of length or modification (e.g., acetylation or ionization). A glycan can be, for example, two or more monosaccharide molecules, one or more monosaccharide molecules covalently linked to a lipid, one or more monosaccharide molecules covalently linked to a polypeptide, or one or more monosaccharide molecules covalently linked to a complex structure of other saccharide units.

Biological samples that can be used in the methods described herein include, without limitation, samples of bodily fluid such as blood, plasma, serum, urine, saliva, sputum, induced sputum, nasal washing, bronchial washing, bronchial brushing, tracheal secretions, bronchoalveolar lavage, and cerebrospinal fluid. The volume of a biological sample can range from about 0.02 mL to about 200 mL, or any amount or range there between (e.g., about 0.02 mL to about 0.5 mL, about 0.5 mL to about 1 mL, about 1 mL to about 3 mL, about 3 mL to about 10 mL, about 10 mL to about 100 mL, or about 100 mL to about 200 mL).

The biological sample can be contacted with one or more immobilized lectins or antibodies (e.g., on a lectin affinity column or lectin-linked magnetic particles), in order to enrich or purify *Coccidioides* antigens (e.g., peptides and/or glycans) that may be in the biological sample. In some embodiments, the biological sample can be incubated with one or more lectins for up to 48 hours (e.g., from about 1 second to about 48 hours, about 1 second to about 60 seconds, about 1 minute to about 5 minutes, about 5 minutes to about 10 minutes, about 10 minutes to about 30 minutes, about 30 minutes to about 60 minutes, about 1 hour to about 3 hours, about 3 hours to about 6 hours, about 6 hours to about 12 hours, about 12 hours to about 24 hours, or about 24 hours to about 48 hours).

The one or more lectins with which the biological sample is contacted can include one or more (e.g., one, two, three, four, five, two or more, three or more, four or more, or five or more) of the following: wheat germ agglutinin (WGA), succinylated WGA (sWGA), *Griffonia simplicifolia* II lectin (GSLII), Concanavalin A (Con A), *Erythrina* crystagalli Lectin (ECL), and *Pisum sativum* Agglutinin (PSA). In some embodiments, one or more lectins selected from Con A, *Datura stramonium* lectin (DSL), ECL, *Griffonia simplicifolia* lectin I (GSLI), Jacalin (JAC), Len *culinaris* lectin (LCA), peanut agglutinin (PNA), *Phaseolus vulgaris* erythroagglutinin (PVE), *Phaseolus vulgaris* leukoagglutinin (PVL), PSA, *Ricinus communis* agglutinin (RCA I), *Solanum tuberosum* lectin (STL), soybean agglutinin (SBA), *Ulex europaeus* agglutinin I (UEA I), and *Vicia villosa* lectin (VVL) may bind to human glycans in the biological sample, thus enriching *Coccidioides* polypeptides by reducing the number or percentage of free human glycoproteins or free glycans present in the biological sample.

*Coccidioides* antigens can be detected using any suitable method. Mass spectrometry can be particularly useful, however. As noted above, mass spectrometry has a high analytical specificity since specific mass/charge peaks typically are highly reproducible. Thus, mass spectrometry can be used to generate mass/charge peaks representative of antigens from the *Coccidioides* fungus. In some embodiments, matrix associated laser desorption ionization time of flight (MALDI-TOF) mass spectrometry or liquid chromatography followed by tandem mass spectrometry (LC-MS/MS) can be used.

It is to be noted that this document also contemplates detection and diagnosis of conditions associated with other types of fungi, such as *Blastomyces* sp., *Histoplasma* sp., *Aspergillus* sp., *Candida* sp., and *Mucor* sp., for example. Thus, using a lectin column and doing a glycan extraction by mass spectroscopy as described herein for *Coccidioides*, biomarkers as defined by certain mass/charge peaks specific for other genera of fungi (e.g., *Histoplasma* and *Blastomyces*) can be detected, and subjects can be diagnosed and treated effectively.

The invention will be further described in the following examples, which do not limit the scope of the invention described in the claims.

EXAMPLES

Example 1—Lectin Reactivity to *Coccidioides* in Infected Lung Tissue and Demonstration of GSLII and sWGA Binding to Coccidioidal Proteins Methods Lectin-Based Immunohistochemistry (IHC):

IHC was performed using formalin-fixed paraffin embedded (FFPE) blocks obtained from patients with VF. Five (5) µm tissue sections from seven patients who underwent either lobectomy, wedge resection, or excisional biopsy from a skin lesion (wrist) were used for IHC. Tissue sections on slides were blocked in Alkaline Phosphatase/Horseradish Peroxidase Block (SurModics, Cat #APHP-0111-01) for 15 minutes, followed by Carbo-Free Blocking Solution (Vector Laboratories, Cat #SP-5040) for 1 hour. Biotinylated lectins were obtained from Vector Laboratories (Cat #B-1215, B-10255). Preliminary experiments were performed to optimize the lowest concentration of lectin that showed positive staining, which was 2 µg/ml for both GSLII and sWGA. Biotinylated lectins bound to tissue sections were detected with streptavidin (SA) coupled to horseradish peroxidase (HRP) using Diaminobenzidine (DAB) as substrate. Sections were washed with 1×PBS (3 times for 5 minutes each) between blocking, incubation with lectin, detection with SA-HRP, and staining with DAB. Tissue was counterstained using hematoxylin (Santa Cruz Cat #SC-24973). GSLII and sWGA were inhibited with serial dilutions of chitin hydrolysate, a concentrated solution of GlcNAc (Vector Labs, Cat #SP-0090). *Phaseolus vulgaris* erythrolectin (PVE), a lectin that binds Galβ4GlcNAcβ2Manα6, was used as a negative lectin control.

Figure 3:
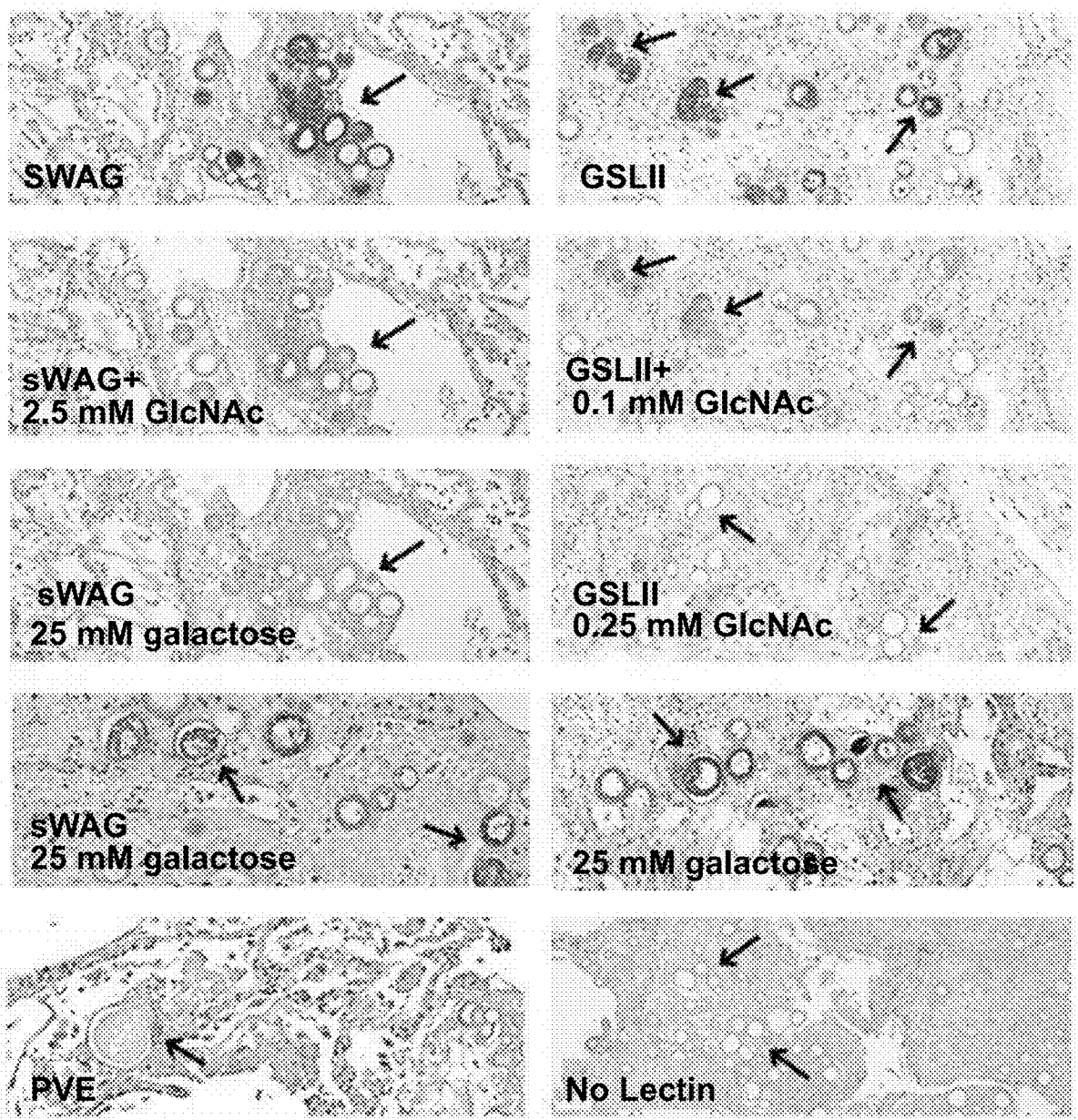
FIG. 3 contains lectin-based IHC micrographs. Biotinylated lectins were incubated with infected lung tissues, as indicated. Darker areas indicate reactivity of lectin. Spherules are larger round structures with or without endospores inside. Arrows indicate examples of spherules or groups of spherules. GlcNAc-mediated inhibition of sWGA and GSLII binding to spherules and endospores is shown at different dilutions. Galactose did not inhibit binding of either lectin to spherules. PVE did not bind the spherules, but did bind to human lung tissue.

Inhibition of Lectin-Based IHC:

To support the hypothesis of lectin-like binding to spherules and endospores, reactivity of GSLII and sWGA was inhibited in a concentration-dependent manner with commercial solution of monomeric and oligomeric GlcNAc (100 mM). A high concentration of GlcNAc (1:4 dilution; 25 mM) was required to completely inhibit sWGA binding to the spherules, while a relatively lower amount of GlcNAc (1:400 dilution; 0.25 mM) inhibited GSLII binding, suggesting that sWGA binding to spherules and endospores is stronger than GSLII (FIG. 3). When galactose (non-specific sugar) was used to inhibit the binding of these two lectins to the fungal spherules, there was a complete lack of inhibition.

Lectin-Based Inhibition EIA:

Spherulin was coated onto a flat-bottom 96 well microtiter plate at 1 µg/ml in PBS for one hour at room temperature. Wells were blocked with 1% carbo-free BSA in PBS for an additional hour. Two-fold (starting from 1 µM) dilutions of non-biotinylated sWGA and GSLII were used to challenge the binding of biotinylated GSLII and sWGA, respectively. For instance, non-biotinylated sWGA was incubated with biotinylated GSLII for 10 minutes prior to placement on the plate. Non-biotinylated lectin dilutions started at 1 µM, and biotinylated lectins were held constant at 10 nM. The mixture was then added to the plate for one hour. PVE was used as a negative lectin control. Bound lectins were detected with a 5000-fold dilution of SA-HRP (Thermo-Pierce, Cat #21130) in PBS. Plates were washed three times with PBS containing 0.05% Tween-20 (PBST) between coating, blocking, incubation with lectin, detection with SA-HRP, and addition of 3,3',5,5'-Tetramethylbenzidine (TMB) (Becton-Dickinson, Cat #555214). 1N $H_2SO_4$ was used to stop the HRP enzyme, and the plate was read in a Molecular Diagnostics plate reader at 450 nm using SoftmaxPro software. The percent of control was calculated using the following formula: $(OD_{biotinylated\ lectin\ in\ presence\ of\ non-biotinylated\ inhibitor})/(OD_{biotinylated\ lectin\ in\ the\ absence\ of\ inhibitor}) \times 100 =$ percent of control.

Results

Twenty-one lectins were tested for their reactivity to *Coccidioides* spherules and endospores in infected human lung tissue, using lectin-based immunohistochemistry (IHC). *Coccidioides*-binding lectins identified in these studies were confirmed and tested for their ability to bind to laboratory-grown *Coccidioides* using a lectin-based enzyme-linked immunosorbent assay (EIA). Known binding properties (sugar specificities) of *Coccidioides*-binding lectins were then confirmed using both IHC and EIA inhibition assays.

The lectins tested for binding to *Coccidioides* spherules are listed in TABLE 1. Representative micrographs indicating binding patterns for certain lectins (Con A, GSLII, PVE, and sWGA) are shown in FIG. 1. Two of these (GSLII and sWGA) exhibited specific staining of spherules and endospores, and did not bind to adjacent lung tissue. Other lectins, such as PVE, bound to lung tissue but not to spherules and endospores, while ConA, in particular, bound spherules, endospores and adjacent tissue. The binding properties of GSLII and sWGA was confirmed with seven patients, showing the specific binding to *Coccidioides* was common among different individual patients' coccidioidal infections and different and tissues (FIG. 2).

Both GSLII and sWGA have known specificity for GlcNAc. When these lectins were pre-incubated with chitin hydrolysate (GlcNAc) prior to addition to infected lung tissue, binding of both sWGA and GSLII to spherules and endospores was inhibited (FIG. 3). These experiments indicated that sWGA and GSLII interact with GlcNAc groups on fungal proteins. Galactose did not inhibit binding.

Figure 4A:
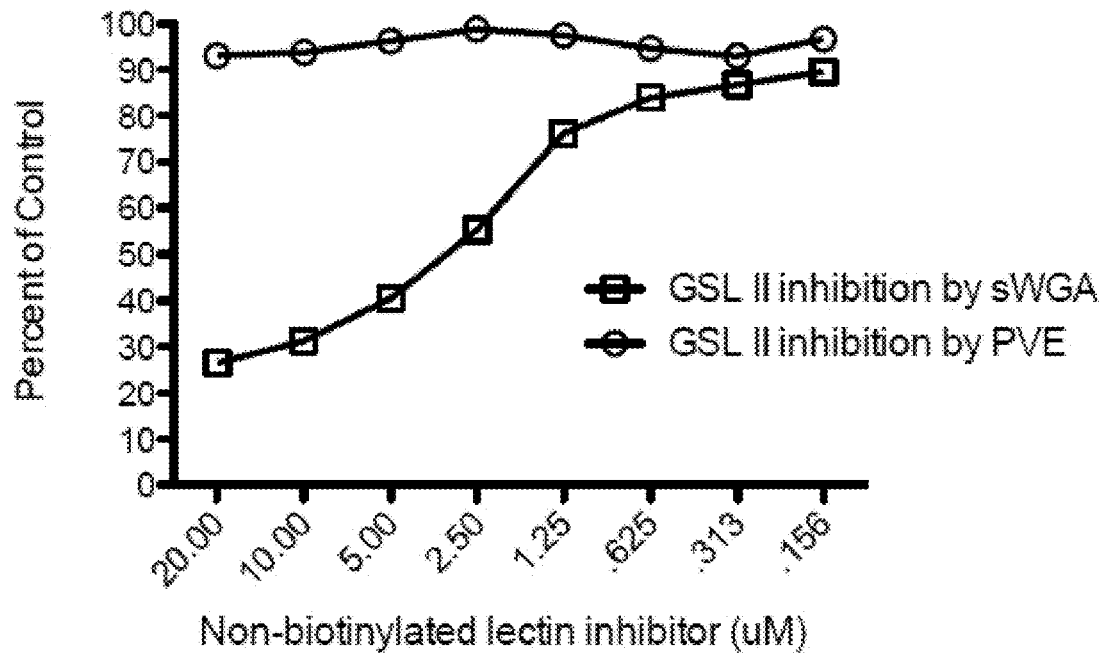
FIGS. 4A and 4B are graphs plotting the binding of GSLII (FIG. 4A) and sWGA (FIG. 4B) to spherules in the presence of decreasing concentrations of inhibitors, as indicated. Two-fold dilutions of non-biotinylated sWGA and GSLII lectins starting at 20 μM were incubated in an EIA plate coated with Spherulin for 20 minutes. Biotinylated GSLII or sWGA was added and incubated for one hour. After washing the plate, streptavidin-HRP was added to detect biotinylated lectins that were not inhibited from binding to Spherulin. After TMB substrate development, the plate was read at 450 nm. The percent of control binding ($OD_{biotinylated\ lectin\ in\ with\ non\text{-}biotinylated\ inhibitor}/OD_{biotinylated\ lectin\ without\ inhibitor} \times 100$) is plotted.
Figure 4B:
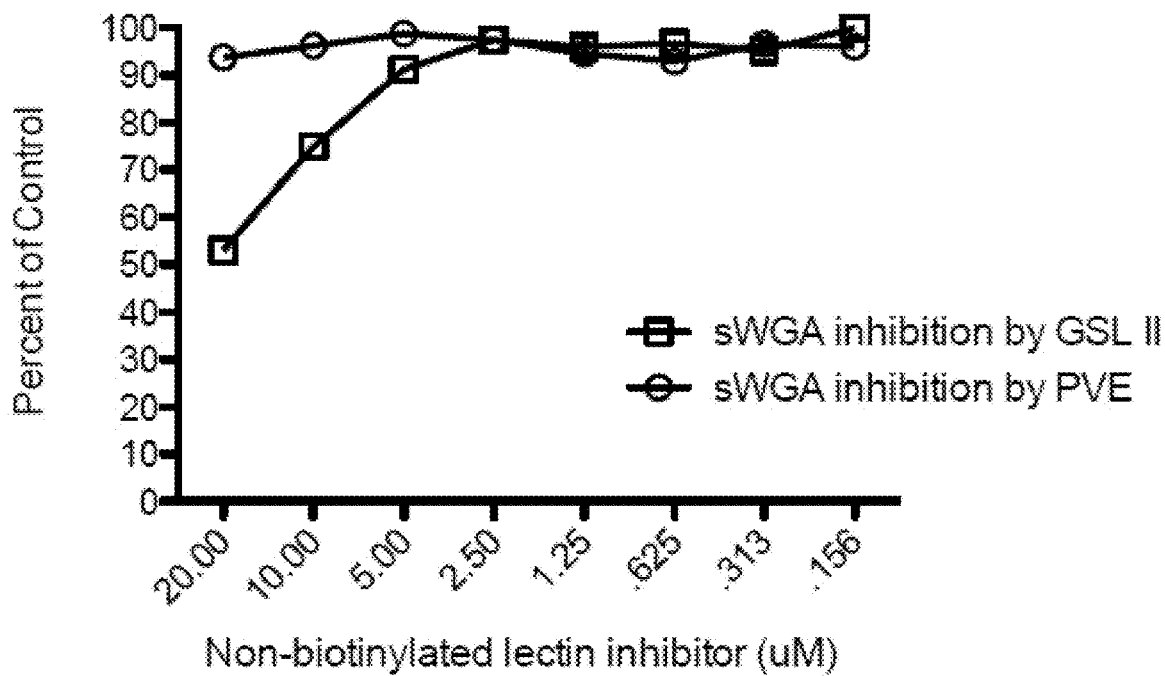

To confirm the lectin-based IHC results and assess whether sWGA and GSLII compete for the same glycan structure, an inhibition EIA was performed on Spherulin coated plates using biotin-GSLII and biotin-sWGA as detection agents. As shown in FIGS. 4A and 4B, sWGA inhibits binding of biotinylated GSLII to Spherulin in a concentration-dependent manner, with a relative IC50 of 1.5 µM. In contrast, 50% inhibition of 1 nM biotinylated sWGA was not reached with GSLII, even at 20 µM, suggesting higher avidity of sWGA for GlcNAc on coccidioidal glycoproteins than GSLII. PVE, a Galβ4GlcNAcβ2Manα6 binding lectin, did not inhibit either GSLII or sWGA, and served as a "control" lectin.

Taken together, these studies identified lectins that bind specifically to *Coccidioides* spherules and endospores in infected humans, and showed in particular that GSLII and sWGA, two GlcNAc-binding lectins, bind specifically to coccidioidal glycoproteins in spherules and endospores present in infected human lung tissue, and bind specifically to proteins in laboratory grown *Coccidioides* spherules. Interestingly, only two of the five GlcNAc-binding lectins tested (GSLII, sWGA, DSL, LEL, and STL) bound specifically to spherules and endospores in lung tissue, suggesting that the affinity-purified glycoproteins have terminal GlcNAcs or specific glycan linkages that may be involved in their binding specificities. The most abundant lectin affinity-purified glycoproteins from *Coccidioides* are involved in growth and metabolism of the fungus.

TABLE 1

Lectins tested, their known sugar specificities, and their reactivity in infected human lung tissue. Bolded lectins exhibited specific staining of spherules and endospores.

| Lectin | Sugar Specificity | Reactivity in Infected Lung Tissue |
| --- | --- | --- |
| Concanavalin A (Con A) | Mannose | Spherules, endospores, and lung tissue |
| *Datura stramonium* Lectin (DSL) | N-Acetylglucosamine, | Lung tissue |
| *Dolichos bijlorus* Agglutinin (DBA) | N-Acetylgalactosamine | No reactivity |
| *Erythrina crystagalli* Lectin (ECL) | Galactose | Spherules and lung tissue (some reactivity) |
| *Griffonia simplicifolia* Lectin I (GSL I) | Galactose | Not fully characterized |
| Griffonia simplicifolia Lectin I (GSL II) | N-Acetylglucosamine (GlcNAc) | Spherules and endospores |
| Jacalin | Galactose | Lung tissue |
| *Len culinaris* Lectin (LCA) | Mannose | Lung tissue (some reactivity) |
| *Lycopersicon esculentum* Lectin (LEL) | N-Acetylglucosamine | No reactivity |
| Peanut Agglutinin (PNA) | Galactose | Lung tissue (some reactivity) |
| *Phaseolus vulgaris* Erythroagglutinin (PVE) | Complex N-glycans | Lung tissue |
| *Phaseolus vulgaris* Leukoagglutinin (PVL) | Complex N-glycans | Lung tissue |
| *Pisum sativum* Agglutinin (PSA) | Mannose | Spherules, endospores, and lung tissue |
| *Ricinus communis* Agglutinin I (RCA I) | Galactose, N-Acetylglucosamine | Lung tissue |
| *Solanum tuberosum* Lectin (STL) | N-Acetylglucosamine | Lung tissue (some reactivity) |
| *Sophora japonica* Agglutinin (SJA) | N-Acetylgalactosamine | No reactivity |
| Soybean Agglutinin (SBA) | N-Acetylgalactosamine | Lung tissue (some reactivity) |
| Succinylated Wheat Germ Agglutinin (sWGA) | N-Acetylglucosamine (GlcNAc) | Spherules and endospores |
| *Ulex europaeus* Agglutinin I (UEA I) | Fucose | Lung tissue (some reactivity) |
| *Vicia villosa* Lectin (VVL) | N-Acetylgalactosamine | Lung tissue (some reactivity) |
| Wheat Germ Agglutinin (WGA) | N-Acetylglucosamine | Spherules and endospores |

Example 2—Spherulin Proteome and Lectin-Binding Glycoproteome of *C. posadasii*

Methods

Preparation of Spherulin: *C. posadasii* (strain Silvera) spherule-phase cells were maintained in continuous culture at 40° C., 20% $CO_2$, with continuous shaking at 120 RPM in modified Converse medium (Cox and Britt, *Infect Immun* 55(11):2590-2596, 1987). In brief, cultures were initiated by seeding flasks of Converse medium with ~1-5×10$^5$ arthrospores/ml. At three to four day intervals, the cells collected by centrifugation, washed in sterile distilled water, and stored at 4° C. in 0.5% formalin in water. Prior to fixing in formalin, the cells were checked by microscopy to ensure that the culture was mixed-phase spherules and endospores by morphology and for purity by culture on glucose-yeast extract agar plates. The spent medium was supplemented to 0.5% formalin and stored at 4° C. The spent medium contained antigens elaborated during cellular growth (Spherulin filtrate, SPH-F). The SPH-F antigens were concentrated using a 10,000 MW ultrafiltration membrane. The collected mixed-phase spherules and endospores were processed to obtain the lysate antigen preparation (Spherulin lysate, SPH-L). To release the internal antigens, the fungal cells were processed in an ice-cooled Beadbeater using 0.5 mm glass beads for 5 minutes. Cellular debris was removed by centrifugation (6,000×g, 10 minutes) and the supernatant collected. Both SPH-F and SPH-L were lyophilized and stored at −80° C. until use. SPH-L and SPH-F were combined in these studies, and are referred to as "Spherulin."

Spherulin Analysis Using LC-MS/MS:

20 µg of Spherulin was suspended in SDS sample loading buffer (50 mM Tris-HCl, pH 6.8, 2% SDS, 10% glycerol, 1% 2-mercaptoethanol, 12.5 mM EDTA and 0.02% bromophenol blue) and heated to 95° C. The proteins were then separated by 12% SDS-PAGE and stained with Bio-Safe Coomassie G-250 Stain. Each lane of the SDS-PAGE gel was cut into six equal size slices, placed in a 0.6-ml polypropylene tube, destained twice with 375 µl of 50% acetonitrile (ACN) in 40 mM $NH_4HCO_3$, and dehydrated with 100% ACN for 10 minutes. After removal of ACN by aspiration, the gel pieces were dried in a vacuum centrifuge at 60° C. for 30 minutes. Trypsin (250 ng; Sigma) in 20 µl of 40 mM $NH_4HCO_3$ was added, and the samples were maintained at 4° C. for 15 minutes prior to the addition of 50 µl of 40 mM $NH_4HCO_3$. Digestion was allowed to proceed at 37° C. overnight and was terminated by addition of 10 µl of 5% formic acid (FA). After further incubation at 37° C. for 30 minutes and centrifugation for 1 minute, each supernatant was transferred to a clean polypropylene tube. The extraction procedure was repeated using 40 µl of 0.5% FA, and the two extracts were combined. The resulting peptide mixtures were purified by solid phase extraction (C18 ZipTip) after sample loading in 0.05% heptafluorobutyric acid:5% FA (v/v) and elution with 4 µl of 50% ACN:1% FA (v/v) and 4 µl of 80% ACN:1% FA (v/v), respectively. The eluates were combined and dried by vacuum centrifugation, and 6 µl of 0.1% FA (v/v) was added, followed by sonication for 2 minutes. The sonicated samples were briefly centrifuged, and 2 µl of the sample was subsequently analyzed by mass spectrometry as described below.

Lectin Affinity Chromatography:

GSLII and sWGA coupled to agarose beads were purchased from Vector Labs (Cat #AL1213 and AL1023S) and used to affinity-purify glycoproteins from Spherulin. 500 µg of Spherulin dissolved in PBS was applied to lectin-agarose columns (0.5 ml bed volume). Spherulin starting material and column flow through were saved for subsequent SDS-PAGE analysis. Ten bed volumes of PBS were used to wash the column of unbound lysate. The last 200 ul of PBS wash was saved for mass spec analysis to ensure that glycoproteins were not non-specifically washing off the column. Then three bed volumes of "Glycoprotein Eluting Solution for GlcNAc Binding Lectins" (Vector Labs, Cat #ES5100) were used to elute glycoproteins bound to GSLII and sWGA-Agarose. The elutions were collected, and concentrated by ultrafiltration to 50 µl using Amicon Ultra 0.5 ml 3 KDa cutoff centrifugal filters (Cat #UFC500396). Protein content in the concentrated eluates were measured using the Micro BCA Protein Assay Kit (Thermo Pierce, Cat #23235) according to the manufacturer's directions.

Deglycosylation:

Spherulin was deglycosylated using a PNGaseF kit according to the manufacturer's instructions (New England Biolabs, Cat #P0704L). Briefly, 500 µg of Spherulin was denatured using 10× glycoprotein denaturation buffer at 95° C. for 5 minutes, followed by 5 minutes on ice. For deglycosylation, 10×G7 Reaction Buffer, 10% NP40, and PNGase were added and allowed to incubate for 6 hours at 37° C. Deglycosylated Spherulin was applied to lectin bound agarose beads in columns (as above), and eluates were analyzed by SDS-PAGE and digested with trypsin. SDS-PAGE gel bands were prepared for mass spectrometry analysis using the following procedures. Colloidal blue stained gel bands were destained in 50% acetonitrile/50 mM Tris pH 8.1 until clear, and the proteins were reduced with 50 mM TCEP/50 mM Tris pH 8.1 at 55° C. for 30 minutes, followed with alkylation using 20 mM iodoacetamide/50 mM Tris pH 8.1 at room temperature for 30 minutes in the dark. Proteins were digested in situ with 0.15 µg trypsin (Promega Corporation, Madison, WI) in 25 mM Tris pH 8.1/0.0002% Zwittergent 3-16, at 37° C. overnight, followed by peptide extraction with 2% trifluoroacetic acid and acetonitrile. The pooled extracts were concentrated and the proteins were identified by nano-flow liquid chromatography electrospray tandem mass spectrometry (nanoLC-ESI-MS/MS) using a Thermo Scientific Q-EXACTIVE PLUS™ Mass Spectrometer (Thermo Fisher Scientific; Bremen, Germany) coupled to a Thermo ULTIMATE™ 3000 RSLCnano HPLC system.

Mass Spectrometry:

Peptides present in each sample were loaded onto a 0.25 µL bed OPTIPAK® trap (Optimize Technologies; Oregon City, OR) custom-packed with 5 µm, 200 A Magic C18 stationary phase. The loaded trap was washed for 4 minutes with an aqueous loading buffer of 0.2% FA and 0.05% TFA at 10 µL/minute. Following the wash, peptides were transferred onto a 35 cm×100 µm PICOFRIT® column, self-packed with Agilent Poroshell 120S 2.7 µm EC-C18 stationary phase, using a Dionex ULTIMATE® 3000 RSLC liquid chromatography (LC) system (Thermo; San Jose, CA). Peptides were separated using a 400 nL/minute LC gradient comprised of 2%-40% B in 0-70 minutes. Mobile phase A was 2% acetonitrile (ACN) in water with 0.2% FA, and mobile phase B was ACN/isopropanol/water (80/10/10 by volume) with 0.2% FA. Eluting peptides were analyzed using a Q-EXACTIVE PLUS™ mass spectrometer (Thermo-Fisher, Waltham, MA). The instrument was configured to operate in data-dependent mode by collecting MS1 data at 70,000 resolving power (measured at m/z 200) with an AGC value of 1E6 over a m/z range of 360-2000, using lock masses from background polysiloxanes at m/z 371.10123 and 446.12002. Precursors were fragmented with normalized collision energy (NCE) of 28, fragments measured at 17,500 resolving power and a fixed first mass of 140. Resulting tandem mass spectra (MS/MS) were collected on the top 20 precursor masses present in each MS1 using an AGC value of 1E5, max ion fill time of 50 ms, and an isolation window of 1.5 Da. All raw data files were transcoded into mzML format using msConvert tool of the ProteoWizard library (PMID: 18606607).

Bioinformatics:

A composite protein sequence database was compiled to identify the *Coccidioides* proteins present in the lysate. This database contained *Coccidioides* proteomes obtained from the Broad Institute's *Coccidioides* Genomes project (Neafsey et al., *Genome Res* 20(7):938-946, 2010; and Sharpton et al., *Genome Res* 19(10): 1722-1731, 2009), SwissProt and RefSeq. RefSeq human and bovine proteomes were added to this database to prevent misidentification of proteins originating from cell culture and other human contamination as *Coccidioides* proteins. Common contaminants (wool, cotton, etc.) were added to the database to account for sample handling artifacts. Reversed protein sequences were appended to the database to estimate protein and peptide identification false discovery rates (FDRs).

The MyriMatch (Tabb et al., *J Proteome Res* 6(2):654-661, 2007) (version 2.1.38) database search engine was used to match the MS/MS present in each data file against the composite protein sequence database. The software was configured to use 10 ppm m/z tolerance for both precursors and fragments while performing peptide-spectrum matching. The software derived semitryptic peptides from the sequence database while looking for the following variable modifications: carbamidomethylation of cysteine (+57.023 Da.), oxidation of methionine (+15.994 Da.), and formation of N-terminal pyroglutamic acid (−17.023 Da.). IDPicker (version 3.0.504) software filtered the peptide-spectrum matches at 2% FDR. The software was configured to use an optimal combination of MVH, mzFidelity and XCorr scores for filtering. Protein identifications with at least two unique peptide identifications were considered to be present in the sample. Resulting proteins were clustered into groups of proteins that match the same set of peptides.

Results

Mass Spectrometric Identification of Proteins in Unfractionated Spherulin:

Given the results from the IHC and EIA using Spherulin as antigen, the first step in the lectin-binding proteomic analysis of *Coccidioides* was to identify the complete proteome of Spherulin. Three different *Coccidioides* databases (SwissProt, RefSeq, and Broad Institute's *Coccidioides* Genomes project (Neafsey et al., supra; and Schiess et al., *Mol Oncol* 3(1):33-44, 2009) were employed to search the MS/MS spectra derived from Spherulin. A total of 1390 proteins were identified in Spherulin. A listing of the ten most abundant coccidioidal proteins in Spherulin with high tryptic fragment coverage is shown in TABLE 2. All of these proteins have an effective FDR of 0.0%. Eight of the top ten identified proteins in Spherulin are metabolic enzymes important for fungal growth. The second most abundant Spherulin protein identified is a "conserved hypothetical protein" (CPSG_03975) with a pentapeptide (PT) repeat sequence, and has high homology with an exoprotein involved in adhesion. This finding indicated that CPSG_03975 is no longer "hypothetical" and is highly abundant during fungal growth in vitro. In total, 434 hypothetical proteins were identified, constituting 31% of the total proteins entries in the proteome of Spherulin.

Other highly abundant proteins found in Spherulin were 5-methyltetra-hydropteroyltriglutamate-homocysteine methyltransferase (MET-E; CPSG_03208), Heat shock protein 90 (CPAG_06539), 3-isopropylmalate dehydrogenase (CPAG_08709), glucose-6-phosphate isomerase (CPAG_05681), enolase (CPAG_04681) and fructose biphosphate aldolase (CPAG_09270).

Figures 5A, 5B:
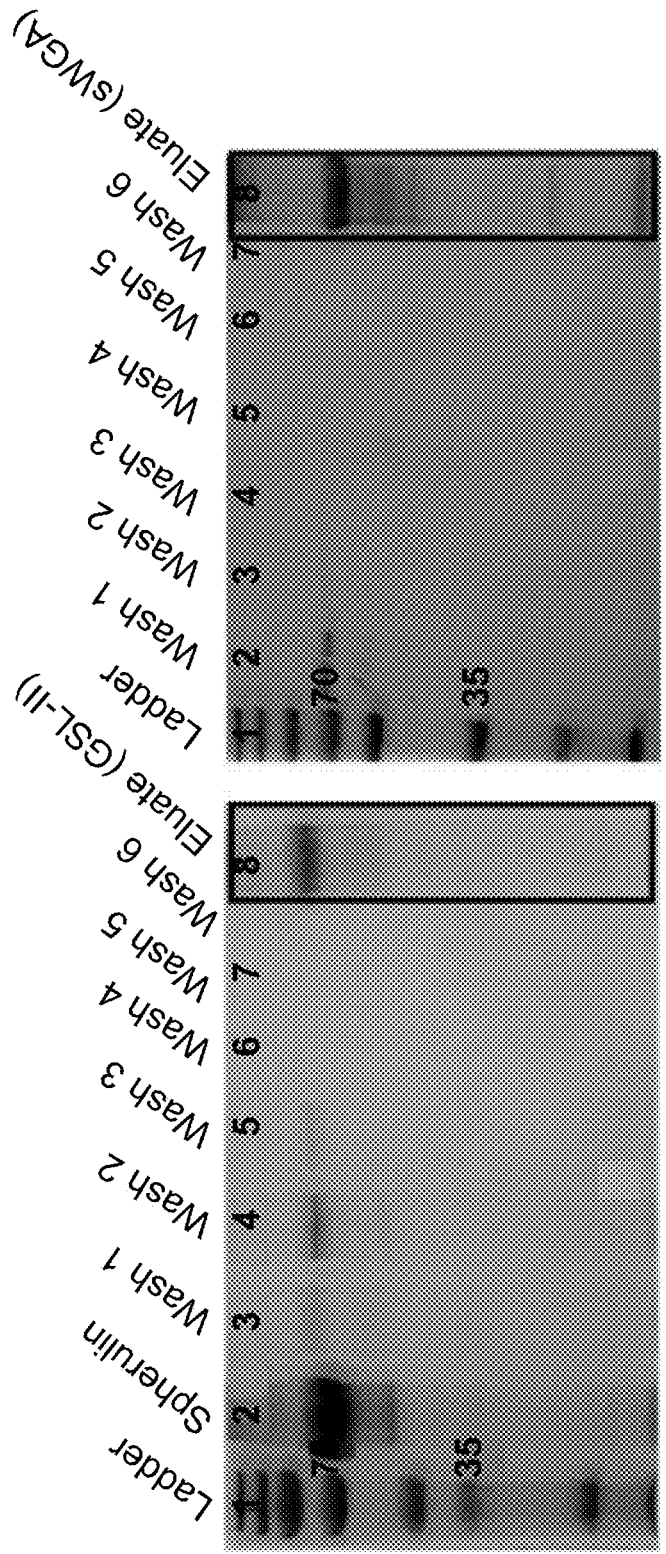
FIGS. 5A and 5B are pictures of SDS-PAGE from GSLII (FIG. 5A) and sWGA (FIG. 5B) lectin columns. Spherulin was used as the starting material prior to running the column. Washes 1-6 represent six 0.5 ml PBS washes collected from the column (the column bed volume was 0.2 ml). The right lane in each gel contains eluted glycoproteins that bound to the lectin column and were eluted using "Glycoprotein Eluting Solution" (Vector Labs). The GSLII and sWGA elution lanes were sliced and processed for trypsin digestion and subsequent mass spectrometry analysis.
Figure 6:
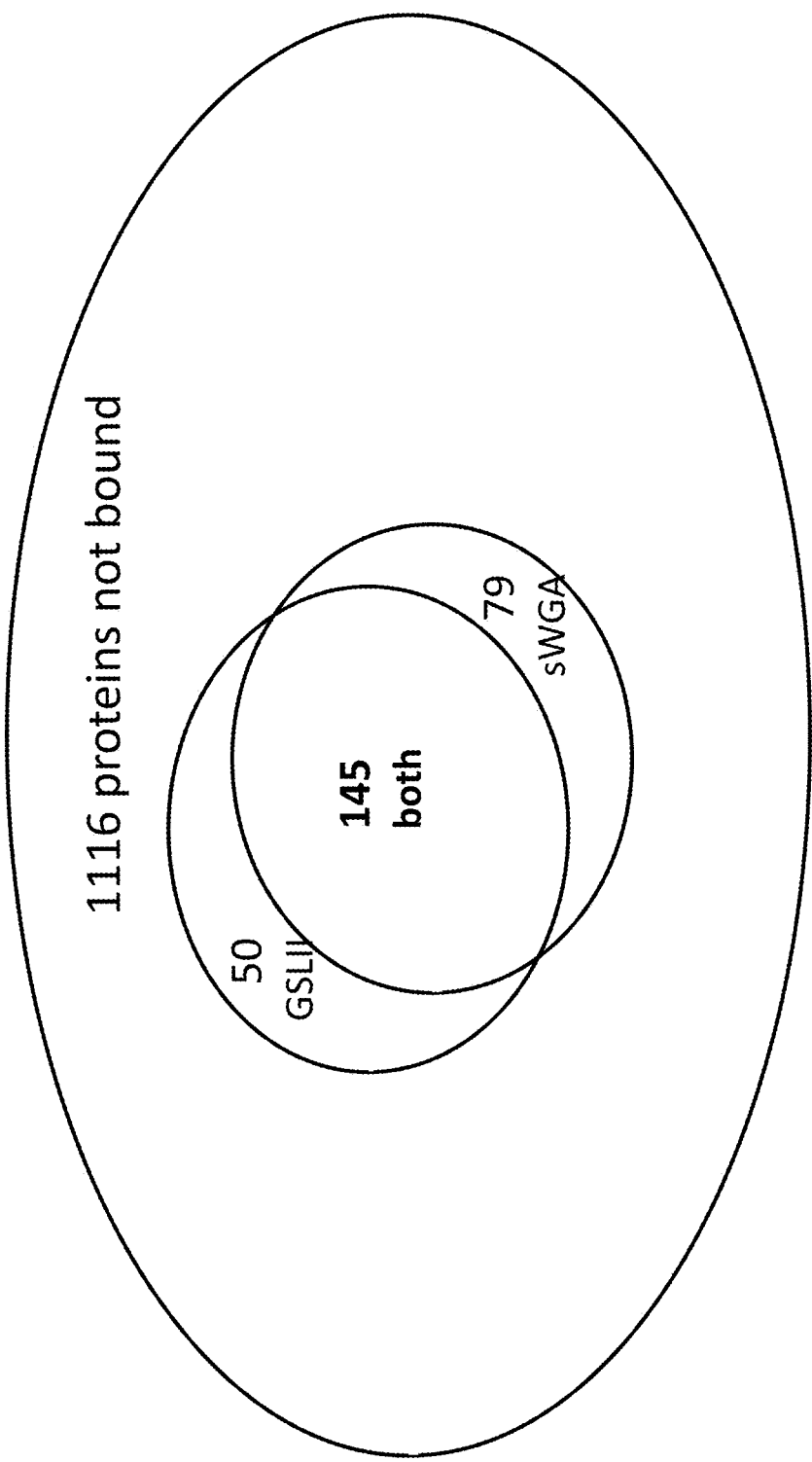
FIG. 6 is a Venn diagram indicating the total and common proteins identified in the GSLII and sWGA lectin column eluates. 145 proteins bound both lectins; a total of 195 proteins bound to GSLII, and a total of 224 proteins bound to sWGA. All glycoproteins in the GSLII fraction were subsets of whole Spherulin and sWGA, and all glycoproteins in the sWGA fraction were subsets of whole Spherulin and GSLII. The proteins that were affinity purified on the two lectin columns represent subsets of the Spherulin proteome.

SDS-PAGE and Identification of Proteins from GSLII and sWGA Affinity Purified Spherulin Eluates:

GSLII and sWGA lectins bind to spherules and endospores in infected human lung tissue sections. Since the principle component of chitin is GlcNAc, it was possible that the lectins simply bound to chitin. However, it also was possible that GlcNAc structures are present on coccidioidal glycoproteins and are accessible to the lectins. Lectin-affinity chromatography of Spherulin, followed by SDS-PAGE, was conducted to determine if there were any glycoproteins that bound to GSLII and sWGA lectins. After Spherulin was loaded onto GSLII and sWGA columns, they were washed extensively and eluted with "Glycoprotein Eluting Solution." The eluted material was dialyzed, concentrated and quantified as described above. FIGS. 5A and 5B show SDS-PAGE gels of Spherulin elution profiles from GSLII and sWGA columns, respectively. Mass spectrometric analysis of Wash 6 (FIGS. 5A and 5B) from the GSLII and sWGA columns did not reveal any coccidioidal proteins, indicating that the remaining material bound to the lectin columns was specific for lectin.

To identify the lectin-binding glycoproteins in Spherulin, the lectin-chromatography enriched glycoproteins were identified using tandem mass spectrometry and analysis of MS/MS spectra. In addition, an analysis was conducted to determine if the enrichment by lectin chromatography enabled detection of additional glycoproteins not identified in whole Spherulin. Searching spectra from tryptic peptides against the *C. posadasii* (strain Silviera) databases (The Broad Institute's *Coccidioides* Genomes project, RefSeq, and SwissProt) revealed that 195 coccidioidal glycoproteins bound to GSLII (FDR of 1.11%), while 224 glycoproteins bound to sWGA (FDR of 1.01%). A total of 145 fungal glycoproteins bound to both GSLII and sWGA lectins (FIG. 6). The ten most abundant coccidioidal glycoproteins eluted from both the GSLII and sWGA lectin columns (highest tryptic peptide coverage) are listed in TABLE 3. The table also lists the percentage peptide coverage for these proteins as well as the unique peptide count for each of the replicate runs from GSLII and sWGA columns. Many hypothetical proteins also were identified in the lectin affinity analysis (36 in the GSLII analysis and 54 in the sWGA analysis). A highly abundant hypothetical protein (CPSG_01012), different from the hypothetical protein identified in whole Spherulin (see below), bound to both lectins. This hypothetical protein has 70% sequence similarity to a ribonuclear protein binding domain protein from *Aspergillus* and other fungi. Other abundant glycoproteins in the lectin analysis included 5-methyltetrahydropteroyl-triglutamate-homocysteine methyltransferase (CPSG_03208), malate dehydrogenase (CPAG_07192), glucose-6-phosphate isomerase (CPAG_05681, and complement fixation-chitinase (CPSG_08657). The lectin-binding glycoproteome constitutes a subset of the proteome derived from Spherulin (FIG. 6).

To further support the evidence that the binding of the lectins was due to GlcNAc structures on proteins, Spherulin was deglycosylated with PNGase F, which cleaves glycans from proteins at asparagine residues (except when there is an α1-3 fucose on the core GlcNAc of the glycoprotein). Deglycosylated Spherulin was run through both GSLII and sWGA columns, followed by SDS-PAGE and trypsin digestion using the methods described above. Mass spectrometry analysis of the PNGase-treated elutions from GSLII and sWGA lectin columns demonstrated nearly complete loss of binding by deglycosylated coccidioidal glycoproteins to the lectin columns (TABLE 3 and FIG. 7). This suggested that the binding of coccidioidal glycoproteins is lectin-like and specific for GlcNAc. Once the glycoproteins were deglycosylated, they no longer bound to the lectin chromatography columns (the eluate profile of deglycosylated Spherulin for sWGA and GSLII affinity columns is shown in lanes 6 and 8, respectively, of FIG. 7).

TABLE 2

Mass spectrometric identification of the top ten coccidioidal proteins in Spherulin (i.e., the ten with the highest number of tryptic peptides).

| Protein ID | % sequence coverage | Unique tryptic peptides identified from Spherulin |
|---|---|---|
| 5-methyltetrahydropteroyltriglutamate-homocysteine methyltransferase (CPSG_03208) | 89 | 188 |
| conserved hypothetical protein (CPSG_03975) | 86 | 89 |
| 3-isopropylmalate dehydrogenase (CPAG_08709) | 91 | 89 |
| malate dehydrogenase (CPAG_07192) | 89 | 89 |
| heat shock protein 90 (CPAG_06539) | 78 | 87 |
| enolase (CPAG_04681) | 77 | 86 |
| fructose biphosphate aldolase (CPAG_09270) | 79 | 78 |
| H538.4 glucose-6-phosphate isomerase (CPAG_05681) | 80 | 78 |
| malate synthase (CPAG_07630) | 71 | 73 |
| fumarate reductase Osm1 (CPSG_05536) | 83 | 70 |

Example 3—Proteomic Analysis of *Coccidioides* Infected Human Lung Tissue, Urine and Plasma with Mass Spectrometry Methods Collection of patient plasma, and urine: Plasma samples were collected from five VF patients, and control plasma was obtained from three healthy blood donors from a non-endemic region (Rochester, MN). The five VF patients were all definitively diagnosed with coccidioidomycosis. Clinical information for the patients follows.

Patient 1: Long term history of VF was reported. At the time of plasma collection for this study, leg lesion and urine cultures grew *Coccidioides*. Serology tests around the time of sample collection also confirmed the diagnosis: CF test was positive with titer of 1:32, IgG positive by ID and EIA. The patient also suffered from rheumatoid arthritis and was on immunosuppressive agents (leflunomide and prednisone).

Patient 2: Patient was diagnosed with disseminated coccidioidomycosis with meningitis, miliary pneumonia, and dissemination to bone at the time of sample collection.

Patient 3: Presented with fatigue, malaise, drenching sweats, non-productive cough, weight loss and dull headache. Left lower lobe of lung showed 2×2 cm nodule and other nodules <4 mm. Diagnostic test results as follows—CSF serology=1:2 CF, EIA positive for both IgM and IgG, ID negative.

TABLE 3

Mass spectrometric identification of top ten coccidioidal glycoproteins in Spherulin that bound to both GSLII and sWGA lectins. CPAG and CPSG numbers denote accession numbers. The number of tryptic peptides in each of three technical replicates for each glycoprotein is shown. "PNGase GSLII" and "PNGase sWGA" indicate that Spherulin was deglycosylated with PNGase prior to lectin affinity chromatography. *Maximum % sequence coverage from all replicates.

| Protein ID | *Max % sequence coverage | Unique peptides in GLSII replicates | | | Unique peptides in sWGA replicates | | | Unique peptides in PNGase GSLII replicates | | Unique peptides in PNGase sWGA replicates | |
|---|---|---|---|---|---|---|---|---|---|---|---|
| | | 1 | 2 | 3 | 1 | 2 | 3 | 1 | 2 | 1 | 2 |
| 5-methyltetrahydropteroyl-triglutamate-homocysteine methyltransferase (CPSG_03208) | 89 | 23 | 16 | 19 | 28 | 15 | 20 | 0 | 0 | 0 | 0 |
| malate dehydrogenase (CPAG_07192) | 89 | 13 | 7 | 10 | 25 | 11 | 11 | 0 | 0 | 0 | 0 |
| fructose biphosphate aldolase (CPAG_09270) | 78 | 12 | 7 | 7 | 15 | 8 | 10 | 0 | 0 | 0 | 0 |
| enolase (CPAG_04681) | 77 | 13 | 9 | 9 | 9 | 8 | 10 | 0 | 0 | 1 | 0 |
| 3-isopropylmalate dehydrogenase (CPAG_08709) | 91 | 13 | 6 | 7 | 12 | 8 | 9 | 0 | 0 | 0 | 0 |
| glucose-6-phosphate isomerase (CPAG_05681) | 76 | 12 | 0 | 5 | 14 | 2 | 3 | 0 | 0 | 0 | 0 |
| aldehyde reductase 1 (CPAG_06394) | 68 | 12 | 4 | 6 | 12 | 5 | 6 | 0 | 0 | 0 | 0 |
| hypothetical protein (CPSG_01012) | 60 | 13 | 10 | 8 | 5 | 2 | 10 | 0 | 0 | 0 | 0 |
| heat shock protein 90 (CPAG_06539) | 62 | 12 | 5 | 2 | 8 | 6 | 8 | 0 | 0 | 0 | 0 |
| complement fixation-chitinase (CPSG_08657) | 75 | 10 | 5 | 4 | 20 | 8 | 9 | 0 | 0 | 0 | 0 |

Patient 4: Patient was diagnosed with peritoneal coccidioidomycosis. Diagnosis was confirmed with serology testing (CF titer at 1:64 at the time of sample collection).

Patient 5: Patient presented with a chronic cough and fatigue with low grade fever. Serologic tests were positive at the time of plasma sample collection (CF titer of 1:32, EIA positive), and findings on chest radiography were consistent with a diagnosis of pulmonary coccidioidomycosis.

Urine samples were collected from Patient 1 and a normal volunteer donor (control urine).

Lectin Affinity Chromatography with Plasma and Urine:

Fifty (50) µl of plasma was ultra-filtered with a 30 kD filter (Millipore, USA) and filtrate was collected. Gravity packed sWGA lectin columns were made with 400 µl slurry. The filtered plasma was diluted with 450 µl of 1×PBS and allowed to bind to the lectin agarose beads for an hour at room temperature with end-on-end shaking. The column was then drained and washed with 5-bed volumes of 1×PBS. Glycoproteins were eluted using an N-acetyl-glucosamine elution buffer (Vector Labs). The eluate was dialyzed and concentrated against 1×PBS using a 3 kD ultra filter.

Five hundred (500) µl urine was centrifuged at 10,000 rpm, and supernatant was collected and filtered with a 0.22 µm filter. The filtered supernatant was then diluted with 1×PBS and applied to a sWGA lectin column as described above.

SDS-PAGE and In-Gel Trypsin Digestion:

SDS-PAGE was performed on lectin enriched samples and bands were prepared for mass spectrometry analysis using the following procedures. Colloidal blue stained gel bands were destained in 50% acetonitrile/50 mM Tris pH 8.1 until clear, and the proteins were reduced with 50 mM TCEP/50 mM Tris pH 8.1 at 55° C. for 30 minutes, followed with alkylation using 20 mM iodoacetamide/50 mM Tris pH 8.1 at room temperature for 30 minutes in the dark. Proteins were digested in situ with 0.15 µg trypsin (Promega Corporation; Madison WI) in 25 mM Tris pH 8.1/0.0002% Zwittergent 3-16, at 37° C. overnight, followed by peptide extraction with 2% trifluoroacetic acid and acetonitrile. The pooled extracts were concentrated and the proteins were identified by nano-flow liquid chromatography electrospray tandem mass spectrometry (nanoLC-ESI-MS/MS) using a Thermo Scientific Q-Exactive Plus Mass Spectrometer (Thermo Fisher Scientific) coupled to a Thermo Ultimate 3000 RSLCnano HPLC system.

Mass Spectrometry:

Tryptic peptides present in each sample were loaded onto a 0.25 µL bed OPTIPAK® trap (Optimize Technologies) custom-packed with 5 µm of 200A Magic C18 stationary phase. The loaded trap was washed for 4 minutes with an aqueous loading buffer of 0.2% FA and 0.05% TFA at 10 µL/minute. Following the wash, peptides were transferred onto a 35 cm×100 µm PICOFRIT® column, self-packed with Agilent Poroshell 120S 2.7 um EC-C18 stationary phase, using a Dionex ULTIMATE® 3000 RSLC liquid chromatography (LC) system (Thermo). Peptides were separated using a 400 nL/minute LC gradient comprised of 2%-40% B in 0-70 minutes. Mobile phase A was 2% acetonitrile (ACN) in water with 0.2% FA, and mobile phase B was ACN/isopropanol/water (80/10/10 by volume) with 0.2% FA. Eluted peptides were analyzed using a QExactive Plus mass spectrometer (Thermo-Fisher). The instrument was configured to operate in data-dependent mode by collecting MS1 data at 70,000 resolving power (measured at m/z 200) with an AGC value of 1E6 over a m/z range of 360-2000, using lock masses from background polysiloxanes at m/z 371.10123 and 446.12002. Precursors were fragmented with normalized collision energy (NCE) of 28, fragments measured at 17,500 resolving power and a fixed first mass of 140. Resulting tandem mass spectra (MS/MS) were collected on the top 20 precursor masses present in each MS1 using an AGC value of 1E5, max ion fill time of 50 ms, and an isolation window of 1.5 Da. All raw data files were transcoded into mzML format using msConvert tool of the ProteoWizard library (Kessner et al., *Bioinformatics* 24(21):2534-2536, 2008).

Bioinformatics:

A composite protein sequence database was compiled to identify the *Coccidioides* proteins present in the lysate. This database contained *Coccidioides* proteomes obtained from the Broad Institute's *Coccidioides* Genomes project, SwissProt and RefSeq (Neafsey et al., supra; and Sharpton et al., supra). RefSeq human and bovine proteomes were added to this database to prevent misidentification of proteins originating from cell culture and other human contamination as *Coccidioides* proteins. Common contaminants (wool, cotton, etc.) were added to the database to account for sample handling artifacts. Reversed protein sequences were appended to the database to estimate protein and peptide identification false discovery rates (FDRs).

MyriMatch (version 2.1.38) database search engine matched the MS/MS present in each data file against the composite protein sequence database (Tabb et al., supra). The software was configured to use 10 ppm m/z tolerance for both precursors and fragments while performing peptide-spectrum matching. The software-derived semitryptic peptides from the sequence database while looking for the following variable modifications: carbamidomethylation of cysteine (+57.023 Da.), oxidation of methionine (+15.994 Da.) and formation of n-terminal pyroglutamic acid (−17.023 Da.). IDPicker (version 3.0.504) software filtered the peptide-spectrum matches at 2% FDR (Kessner et al., supra; and Ma et al., *J Proteome Res* 8(8):3872-3881, 2009). The software was configured to use an optimal combination of MVH, mzFidelity and XCorr scores for filtering. Identified proteins with at least two unique peptide identifications were considered to be present in the sample. The resulting proteins were clustered into groups that matched the same set of peptides.

Results

*Coccidioides* proteins in patient plasma: Both GSLII and sWGA were used in the initial experiments. After 30 kD ultrafiltration and sWGA lectin chromatography, 150 proteins were identified in Patient 1 with tryptic peptides equal to or greater than 1. Among these, at least 2 peptides were identified for 125 different proteins (the number of tryptic fragments per protein ranged from 2 to 26). Using sWGA affinity chromatography enrichment, 125 proteins were identified with 2 or more peptides, and 24 proteins were identified with a single peptide (total 149 proteins).

Patient 2 also had circulating coccidioidal proteins. Using GSLII affinity enrichment, a total of 122 proteins and at least 2 peptides were identified from 64 proteins (the peptide range was 1 to 17). On the other hand, sWGA affinity enrichment of plasma glycoproteins yielded a total of 137 proteins (with a peptide range of 1 to 27). Among these, 97 proteins were identified with at least 2 tryptic fragments. TABLE 4 lists the ten most abundant coccidioidal proteins (those having the highest spectral counts) in patient plasma. Patient 3 had only seven fungal proteins present in plasma, which were identified by two or more tryptic fragments. Patients 4 and 5 had only two and three fungal proteins in circulation, respectively.

Figure 7:
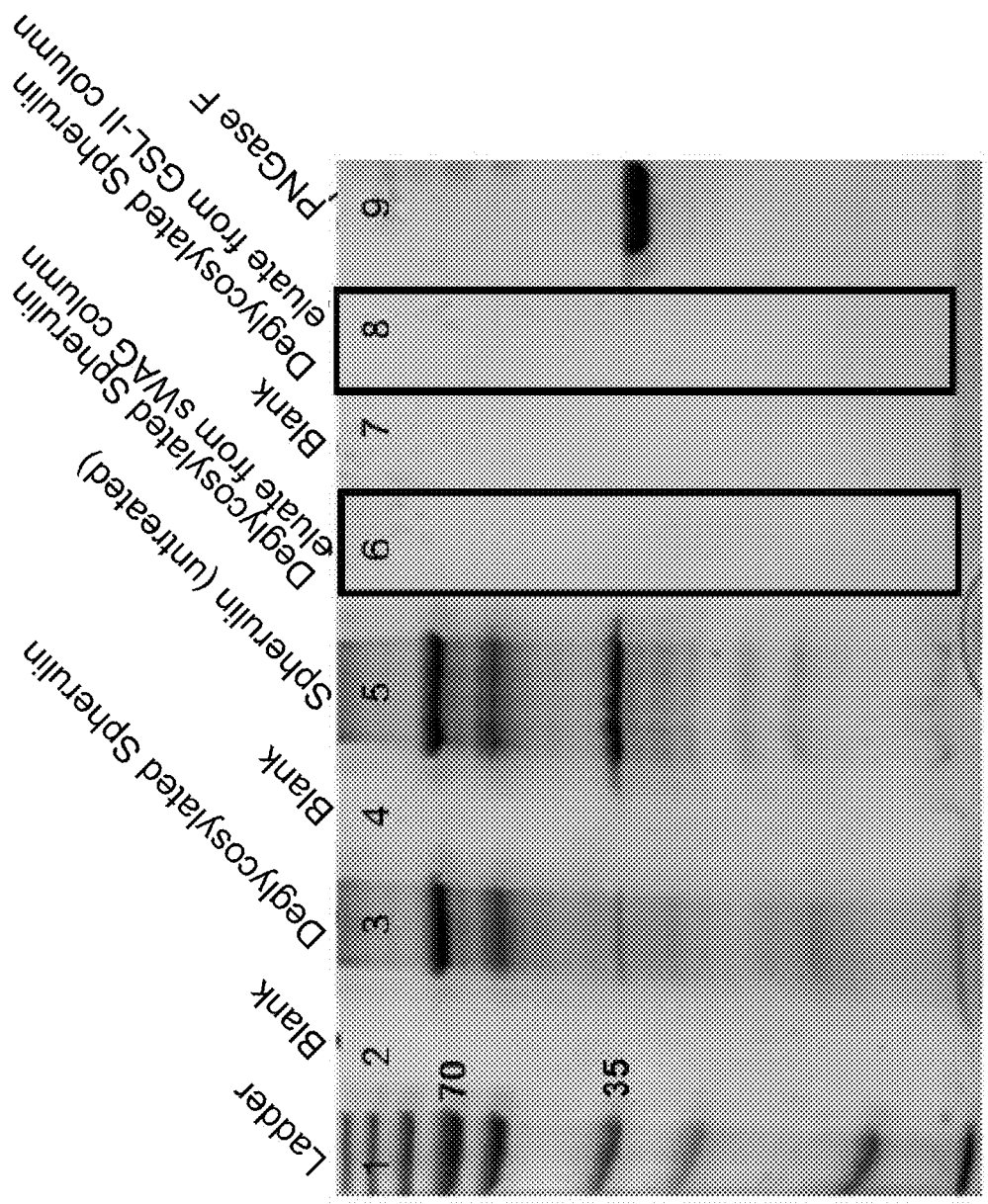
FIG. 7 is a picture of SDS-PAGE showing that treatment of Spherulin with PNGase (an enzyme that removes N-linked glycan chains from proteins) abrogates the binding of GSLII and sWGA lectins. Lanes are numbered and labeled according to treatment. Lanes 6 and 8 (boxed) were cut into gel slices, treated with trypsin, and run on an Orbitrap QExactive mass spectrometer. Spectra were searched using the *Coccidioides posadasii* (Silviera strain). Very few spectra were identified, indicating that lectins were binding glycan on the glycoproteins.

Among the three control plasma samples investigated with both GSLII and sWGA chromatography, single peptides were identified from 6 coccidioidal proteins. A protein identification can be made by the presence of a single tryptic fragment/peptide ("one hit" protein entries), but if the tryptic fragment is not unique to the sequence of that protein, the confidence in identification by mass spectrometry method as in these studies is low. FIG. 7 shows the proteins identified in two patient plasmas based on the presence of at least two tryptic peptides.

*Coccidioides* proteins in patient urine: A urine sample collected from VF patient 1 was enriched for glycoproteins using a sWGA lectin affinity column. The eluate was trypsin digested (in-gel digestion) to reveal the presence of ten coccidioidal proteins. Five of these proteins were identified by single unique peptides, while two or more peptides were identified from three different proteins. Two proteins were identified by the presence of six and five tryptic fragments, respectively. Among the ten proteins thus identified, four also were identified in a "control" urine sample obtained from a healthy donor. This included highly conserved proteins such as actin and ATP synthase. Three proteins were uniquely present in urine from Patient 1 (and absent in plasma). These proteins included ADP ribosylation factor, a GTP binding protein and ATP synthase beta subunit.

TABLE 4

*Coccidioides* proteins identified in patient (n = 2) plasma using sWGA lectin chromatography and LC MS/MS. These fungal proteins were identified in patient plasma (with high spectral and peptide counts) and were absent from control plasma. Percent sequence coverage signifies the extent of tryptic fragments identified from the protein sequence.

| Protein ID | Spectral count | Maximum % coverage | Unique peptides |
|---|---|---|---|
| 5-methyltetrahydropteroyltriglutamate-homocysteine methyltransferase (CPSG_03208) | 283 | 53 | 31 |
| malate dehydrogenase (CPAG_07192) | 162 | 52 | 13 |
| O-acetylhomoserine | 117 | 39 | 12 |
| enolase (CPAG_04681) | 76 | 55 | 15 |
| vacuolar protease A | 72 | 40 | 8 |
| peroxisomal matrix protein | 71 | 64 | 7 |
| endochitinase 1 | 70 | 35 | 12 |
| superoxide dismutase | 59 | 72 | 8 |
| heat shock 70 kDa protein | 54 | 24 | 17 |
| formate dehydrogenase | 51 | 31 | 9 |

Example 4—Lectin Enrichment of *Coccidioides* Glycans in Infected Urine Using Agarose sWGA Column, and Detection by Mass Spectrometry Methods Urine and CDN Ag Collection:

Urine was retrospectively collected from completed diagnostic specimens from the Mayo Clinic Arizona Microbiology Department. Coccidioidin (CDN Ag), a fungal lysate and culture supernatant from in vitro grown mycelia of *Coccidioides posadasii* strain Silveira, was grown as described elsewhere (Grys et al., *J Proteome Res* 15(10): 3463-3472, 2016.)

Urine Lectin Chromatography and Glycan Extraction:

1 ml of urine or 20 µg of CDN Ag was bound for 1 hour at room temperature onto 250 µl sWGA agarose beads (Vector Labs; Burlingham, CA) after equilibrating with ConA buffer pH 8. Beads were washed three times with 2 ml ConA buffer (20 mM Tris, 500 mM NaCl, 1 mM CaCl$_2$, 1 mM MgCl$_2$, pH 7.4) and eluted twice with 250 µl 4M urea pH 4 for 5 minutes each, followed by a 100 µl 0.5% trifluoroacetic acid elution. Six hundred (600) µl of 0.1 M Na$_2$PO$_4$ buffer pH 7.2 was added to neutralize the acid and dilute the urea prior to deglycosylation. Two (2) µL of 2-mercaptoethanol was added to reduce the proteins prior to the addition of 50 U (units) of PNGase F (New England Biolabs; Ipswich, MA) and incubated at 37° C. for 18 hours. The next day, the N-glycans were purified on a Hypercarb porous graphitic carbon (PGC) cartridge (Thermo Scientific; Waltham, MA), according to the manufacturer's instructions.

LC-MS/MS:

Eluted glycans were speed vacuumed until dry and brought up in mobile phase A (0.1% FA in water) and loaded onto a Dionex ULTIMATE® 3000 RSLC liquid chromatography system (Thermo) with a C18 reversed-phase ion trap column. Peptides were separated using a 500 nL/minute LC gradient comprised of 2%-60% B in 0-120 min. Mobile phase A was 2% ACN in water with 0.1% FA and mobile phase B was ACN/methanol/water (80/10/10 by volume) with 0.1% FA. Eluting peptides were analyzed using a Orbitrap Velos mass spectrometer (Thermo-Fisher) using collision-induced dissociation (CID) in positive ion mode. The instrument was configured to operate by data-dependent mode by collecting MS1 data at 60,000 resolving power (measured at m/z 275) with an AGC value of 1E6 over a m/z range of 275-1800. Precursors were fragmented with normalized collision energy (NCE) of 35, and fragments were measured at 17,500 resolving power and a fixed first mass of 275. Resulting tandem MS/MS were collected on the top 20 precursor masses present in each MS1 using an AGC value of 1E5, max ion fill time of 50 ms, and an isolation window of 1.5 Da.

Figure 10A:
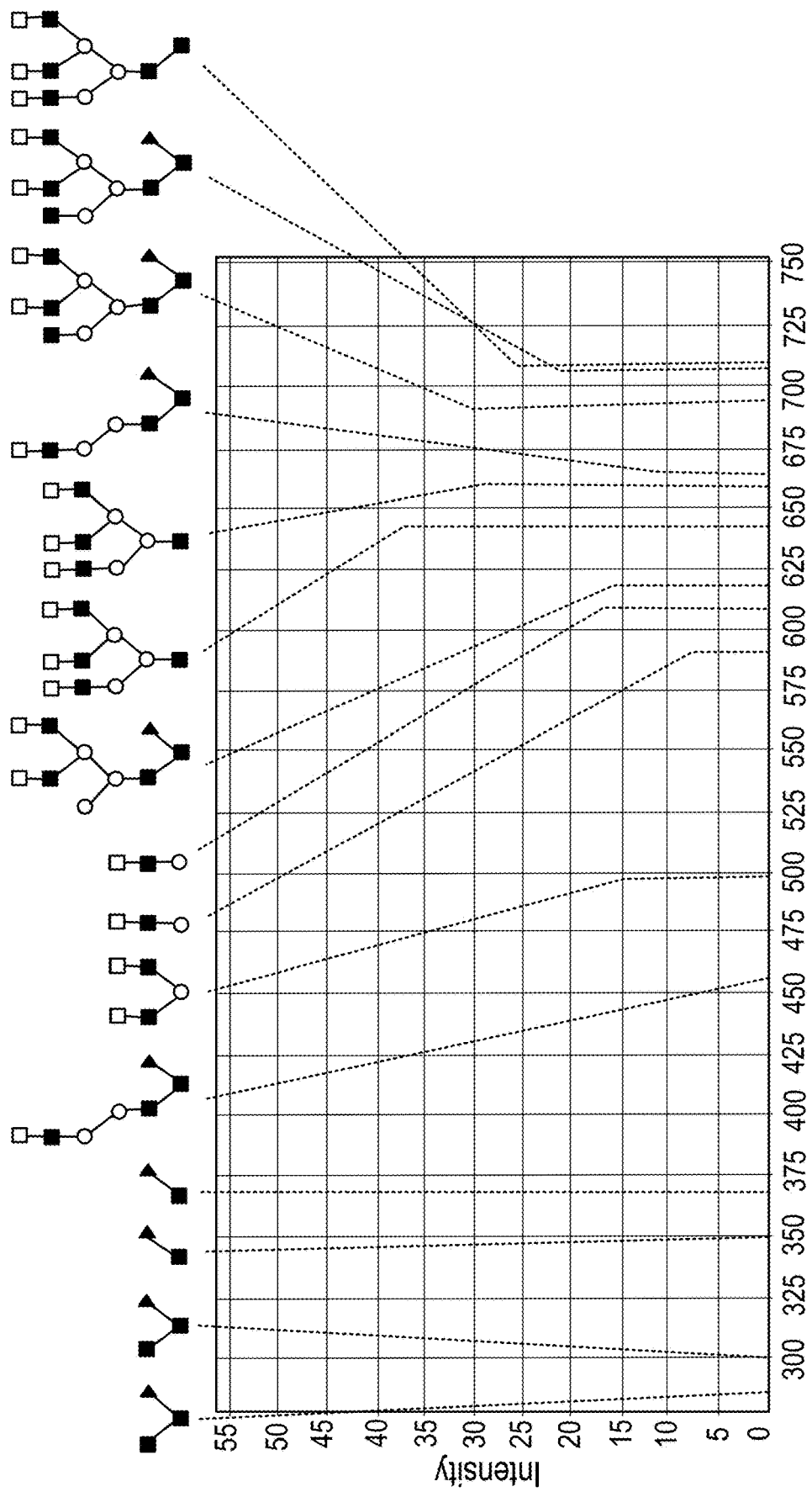
FIGS. 10A-10C show an example of the glycan structure information derived from the precursor m/z value 780.708. All images were acquired in SimGlycan v 5.60.
Figures 10B, 10C:
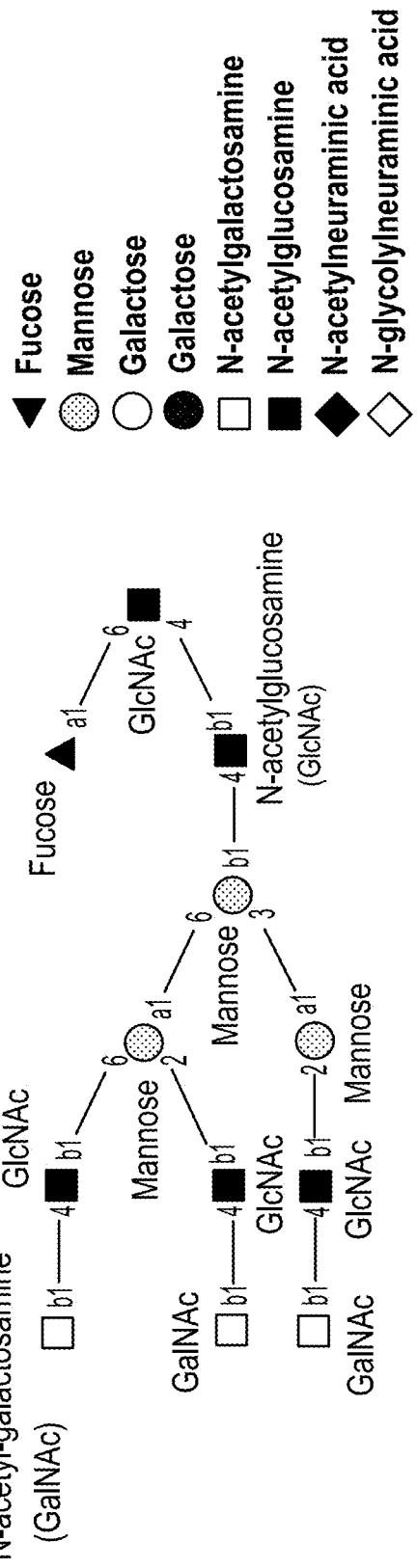

Glycan Analysis and Biomarker Determination:

MS/MS spectra were analyzed using SimGlycan v.5.60 (Premier Biosoft; Palo Alto, CA). Search parameters were underivatized, free glycans in positive ion mode with H and Na adducts. A 1 Da±0.5 Da error tolerance was allowed. All glycosidic and cross-ring cleavage options were set to "yes". Precursor m/z values were analyzed in Venny 2.1 (Oliveros (2007-2015), "Venny. An interactive tool for comparing lists with Venn's diagrams," online at bioinfogp.cnb.csic.es/tools/venny/index.html) to determine shared and unique values amongst the samples. An example of the glycan structure information derived from a particular precursor m/z value is shown in FIGS. 10A-10C.

Results

Based on clinical background, patients were placed into three disease categories (disseminated, acute pulmonary, and chronic pulmonary). Three patients were determined to have disseminated disease, defined as confirmed fungal infection at sites outside the pulmonary cavity; two patients were determined to have acute pulmonary disease, defined as disease confined to the pulmonary cavity with onset less than three months from sample collection; and one patient had chronic pulmonary disease, defined as disease confined to the pulmonary cavity but with active recurring disease and an initial onset of disease greater than one year prior to sample collection. Six negative control urine samples also were included in the data analysis, and were collected from individuals with no symptoms. All results were compared against CDN Ag to determine glycans that also were found in the in vitro grown mycelial phase of the fungus.

There were a number of unique precursor m/z values identified in the different groups that were not found in any of the six negative control urines. As shown in FIG. 9, many possible biomarker glycans were identified, of which some overlap between groups was seen. The first 50 unique precursor m/z values of the glycans found in each group are shown in TABLE 5. Only the first 50 are listed in TABLE 5 due to space constraints, and these are examples of the many biomarkers that can be generated using the approach described herein. These m/z values are specific to the method used, and the same biomarker may produce different m/z values depending on the preparation method and instrumentation differences. However, those m/z values would not be present in subjects who do not have active coccidioidomycosis. In patients of unknown disease state, the detection of biomarkers (via m/z values) that are shared only with patients with proven coccidioidomycosis disease and/or shared with culture lysates of *Coccidioides*, is evidence for diagnosis of coccidioidomycosis.

TABLE 5

The first 50 unique precursor m/z values of glycans found in three Coccidioidomycosis patient categories (acute, chronic, and disseminated), controls, and culture lysates

| Exclusively in Disseminated (n = 45) | Exclusively in Acute Pulmonary (n = 594) | Exclusively in Chronic Pulmonary (n = 16,303) | Exclusively in CDN Ag (n = 13,090) | Common in Disseminated and Acute (n = 6) | Common in Acute and Chronic (n = 6) | Common in Acute, Chronic and CDN Ag (n = 2) | Common in Chronic and CDN Ag (n = 286) | Common in Acute and CDN Ag (n = 84) | Common in Disseminated and CDN Ag (n = 5) | Common in Disseminated, Acute and CDN Ag (n = 3) |
|---|---|---|---|---|---|---|---|---|---|---|
| 1043.49 | 767 | 391.284 | 817 | 1077.7371 | 307.113 | 712.992 | 419.315 | 705 | 317.682 | 302.653 |
| 1246.249 | 1043.769 | 550.7 | 1511 | 394.796 | 317.112 | 499.250 | 1287.001 | 786.401 | 377.228 | 411.212 |
| 322.692 | 969.041 | 542.703 | 718.884 | 457.71 | 573.267 | | 322.822 | 838.372 | 525.289 | 557.297 |
| 333.7 | 1385.89 | 400.74 | 1022.087 | 536.258 | 970.35 | | 786.851 | 811.273 | 540.752 | |
| 344.698 | 823.189 | 590.696 | 516.313 | 716.31 | 482.171 | | 376.899 | 678.323 | 548.75 | |
| 350.68 | 546.838 | 752.6 | 432.225 | 865.908 | 687.323 | | 868.78 | 727.333 | | |
| 393.188 | 1321.946 | 822.432 | 391.885 | | | | 283.263 | 567.788 | | |
| 394.196 | 1264.472 | 1288.9189 | 540.772 | | | | 1056.834 | 701.294 | | |
| 408.71 | 1295.801 | 400.799 | 637.333 | | | | 859.764 | 730.015 | | |
| 409.717 | 960.586 | 489.738 | 583.86 | | | | 982.714 | 520.24 | | |
| 420.181 | 1266.214 | 290.85 | 1149.686 | | | | 737.305 | 419.209 | | |
| 422.251 | 948.789 | 705.591 | 352.531 | | | | 980.686 | 563.774 | | |
| 460.219 | 575.821 | 376.771 | 535.286 | | | | 570.302 | 475.26 | | |
| 462.281 | 951.279 | 406.828 | 344.545 | | | | 1403.6689 | 775.367 | | |
| 492.754 | 1099.725 | 593.157 | 1021.589 | | | | 1160.661 | 693.939 | | |
| 492.755 | 980.1 | 416.794 | 781.365 | | | | 775.826 | 648.284 | | |
| 498.222 | 874.787 | 1435.3621 | 629.354 | | | | 718.322 | 768.359 | | |
| 500.739 | 1000.766 | 422.758 | 567.282 | | | | 1104.1281 | 735.33 | | |
| 511.762 | 1383.705 | 366.805 | 362.518 | | | | 452.87 | 804.862 | | |
| 521.278 | 789.336 | 667.176 | 1062.606 | | | | 1240.04 | 440.226 | | |
| 546.836 | 779.138 | 1320.895 | 1037.069 | | | | 1175.6801 | 833.373 | | |
| 553.317 | 1029.212 | 1533.803 | 1110.613 | | | | 434.882 | 448.203 | | |
| 554.234 | 1168.738 | 566.74 | 1050.593 | | | | 1042.687 | 655.302 | | |
| 570.806 | 1341.635 | 1336.9091 | 1558.905 | | | | 1144.616 | 628.967 | | |
| 578.25 | 1452.635 | 681.693 | 358.534 | | | | 611.806 | 625.296 | | |
| 578.797 | 1280.1071 | 350.81 | 1110.11 | | | | 994.72 | 696.627 | | |
| 595.298 | 1330.099 | 1190.4561 | 694.293 | | | | 986.749 | 586.278 | | |
| 595.81 | 1312.524 | 607.209 | 521.759 | | | | 1078.691 | 702.66 | | |
| 659.341 | 1243.041 | 586.675 | 484.266 | | | | 937.771 | 499.755 | | |
| 661.307 | 343.057 | 1739.684 | 667.36 | | | | 1257.015 | 1029.939 | | |
| 666.794 | 840.724 | 450.799 | 480.8 | | | | 658.826 | 574.795 | | |
| 675.327 | 751.002 | 1759.54 | 727.872 | | | | 712.318 | 804.369 | | |
| 688.268 | 680.968 | 536.164 | 585.798 | | | | 1156.7629 | 743.82 | | |
| 691.381 | 473.237 | 284.832 | 1568.908 | | | | 1034.248 | 645.618 | | |
| 712.837 | 879.873 | 408.768 | 664.397 | | | | 1739.783 | 455.239 | | |
| 714.346 | 586.918 | 1356.827 | 758.489 | | | | 998.447 | 379.191 | | |
| 738.669 | 699.976 | 1602.7581 | 803.427 | | | | 1016.705 | 589.261 | | |
| 776.36 | 908.384 | 454.695 | 443.58 | | | | 697.352 | 768.354 | | |
| 779.366 | 984.316 | 1749.298 | 472.287 | | | | 713.347 | 679.238 | | |
| 780.708 | 957.708 | 448.73 | 361.185 | | | | 801.364 | 646.811 | | |
| 865.611 | 768.997 | 536.675 | 689.875 | | | | 726.011 | 785.705 | | |
| 918.428 | 617.63 | 506.755 | 1000.074 | | | | 627.839 | 356.653 | | |
| 924.99 | 699.315 | 1154.475 | 1102.1071 | | | | 309.063 | 349.659 | | |
| 980.028 | 795.331 | 308.88 | 786.408 | | | | 695.338 | 771.386 | | |
| 980.851 | 655.706 | 1025.058 | 776.912 | | | | 686.424 | 524.757 | | |
| | 732.315 | 522.751 | 1058.582 | | | | 904.954 | 889.388 | | |
| | 447.727 | 504.749 | 622.801 | | | | 789.445 | 732.816 | | |
| | 739.654 | 596.651 | 999.573 | | | | 809.816 | 567.284 | | |
| | 1042.308 | 1479.866 | 711.888 | | | | 744.841 | 796.847 | | |
| | 564.227 | 1205.05 | 1029.08 | | | | 1025.964 | 891.903 | | |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for altering the treatment of a subject receiving immunosuppressive therapy or being considered for immunosuppressive therapy, the method comprising:

enriching for one or more antigens of *Coccidioides immitis* or *Coccidioides posadasii* in a body fluid sample from the subject, wherein the enriching comprises lectin-based enrichment of *C. immitus* or *C. posadasii* antigens, and wherein the lectin comprises succinylated Wheat Germ Agglutinin (sWGA), *Griffonia simplicifolia* II lectin (GSLII), or Wheat Germ Agglutinin (WGA);

detecting one or more of the enriched antigens or polypeptides or glycans therefrom; and stopping or delaying administration of immunosuppressive therapy.

2. The method of claim 1, wherein the immunosuppressive therapy is for solid organ or stem cell transplant.

3. The method of claim 1, further comprising administering to the subject an anti-fungal agent.

4. The method of claim 3, wherein the anti-fungal agent comprises fluconazole, ketoconazole, itraconazole, voriconazole, posaconazole, isavuconazole, or amphotericin.

5. The method of claim 1, wherein the detecting comprises using mass spectrometry.

6. The method of claim 1, wherein the enriching further comprises antibody-based enrichment of *C. immitis* or *C. posadasii* antigens using one or more antibodies against one or more *Coccidioides* antigens.

* * * * *

UNITED STATES PATENT AND TRADEMARK OFFICE
CERTIFICATE OF CORRECTION

| | | |
|---|---|---|
| PATENT NO. | : 12,053,455 B2 | Page 1 of 1 |
| APPLICATION NO. | : 17/333255 | |
| DATED | : August 6, 2024 | |
| INVENTOR(S) | : Thomas E. Grys, Douglas Lake and Natalie Michelle Mitchell | |

It is certified that error appears in the above-identified patent and that said Letters Patent is hereby corrected as shown below:

In the Claims

In Column 25, Line 16, In Claim 1, delete "C. immitus" and insert -- C. Immitis --.

Signed and Sealed this
Twenty-ninth Day of October, 2024

*Katherine Kelly Vidal*

Katherine Kelly Vidal
*Director of the United States Patent and Trademark Office*